(12) United States Patent
Barth et al.

(10) Patent No.: US 11,660,024 B2
(45) Date of Patent: May 30, 2023

(54) METHOD AND SYSTEM FOR ANALYZING HUMAN GAIT

(71) Applicant: Portabiles HealthCare Technologies GmbH, Nuremberg (DE)

(72) Inventors: Jens Barth, Thalmässing (DE); Bjoern Eskofier, Erlangen (DE); Julius Hannink, Nuremberg (DE); Jochen Klucken, Buckenhof (DE); Ralph Steidl, Uttenreuth (DE); Jürgen Winkler, Erlangen (DE)

(73) Assignee: Portabiles HealthCare Technologies GmbH, Nuremberg (DE)

( * ) Notice: Subject to any disclaimer, the term of this patent is extended or adjusted under 35 U.S.C. 154(b) by 719 days.

(21) Appl. No.: 16/308,764

(22) PCT Filed: Jun. 12, 2017

(86) PCT No.: PCT/EP2017/064281
§ 371 (c)(1),
(2) Date: Dec. 10, 2018

(87) PCT Pub. No.: WO2017/216103
PCT Pub. Date: Dec. 21, 2017

(65) Prior Publication Data
US 2019/0150793 A1    May 23, 2019

(30) Foreign Application Priority Data

Jun. 13, 2016  (EP) .................................... 16174268

(51) Int. Cl.
*A61B 5/11*  (2006.01)
*A61B 5/00*  (2006.01)
(Continued)

(52) U.S. Cl.
CPC ............ *A61B 5/112* (2013.01); *A61B 5/6807* (2013.01); *A61B 5/7267* (2013.01); *G06F 3/011* (2013.01);
(Continued)

(58) Field of Classification Search
CPC ..... A61B 5/112; A61B 5/7267; A61B 5/6807; A61B 5/7246; A61B 2562/0219;
(Continued)

(56) References Cited

U.S. PATENT DOCUMENTS 6,522,266 B1 * 2/2003 Soehren ................. G01C 17/00
340/988
6,836,744 B1 * 12/2004 Asphahani ............... A43D 1/02
702/141
(Continued)

FOREIGN PATENT DOCUMENTS

WO    2015/063520    5/2015

OTHER PUBLICATIONS

A. Mannini, D. Trojaniello, U. Della Croce and A. M. Sabatini, "Hidden Markov model-based strategy for gait segmentation using inertial sensors: Application to elderly, hemiparetic patients and Huntington's disease patients," 37th Annual International Conference of the IEEE EMBC (Year: 2015).*

(Continued)

*Primary Examiner* — Lina Cordero
(74) *Attorney, Agent, or Firm* — Lewis & Reese, PLLC

(57) ABSTRACT

The present invention relates to methods for analyzing gait of a subject. In particular, the present invention relates to a method for analyzing gait of a subject, said method comprising: providing data representing the 3D-movement of a foot of said subject over time; identifying within said data first data segments that each represent of at least one stride; determining one or more stride features for each of said first (Continued)

Figure 1:
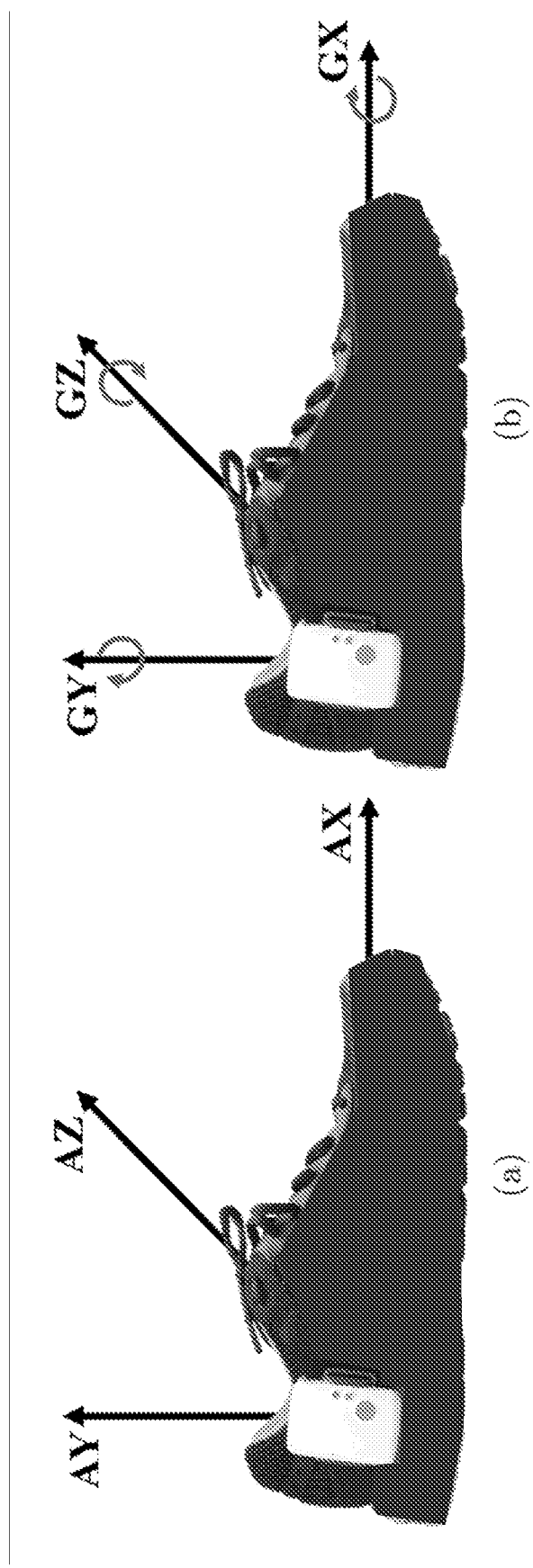

data segments; and defining one or more clusters on the basis of at least one stride feature of said one or more stride features. Each of the defined clusters represents a class of strides, e.g. a class may represent the typical stride of a subject. The present invention also provides for corresponding systems that are configured to perform the methods of the present invention and the use of these systems for analyzing in assessing gait of a subject, preferably a subject suffering from a movement-impairment.

23 Claims, 10 Drawing Sheets

(51) Int. Cl.
　　G06V 40/20　　(2022.01)
　　G06N 20/10　　(2019.01)
　　G06F 3/01　　(2006.01)
　　G06N 3/08　　(2023.01)
(52) U.S. Cl.
　　CPC ............... *G06F 3/017* (2013.01); *G06N 3/08* (2013.01); *G06N 20/10* (2019.01); *G06V 40/25* (2022.01); *A61B 5/7246* (2013.01); *A61B 2562/0219* (2013.01)
(58) Field of Classification Search
　　CPC ...... G06K 9/00348; G06N 20/10; G06N 3/08; G06F 3/011; G06F 3/017; G16H 50/70
　　See application file for complete search history.

(56) References Cited

U.S. PATENT DOCUMENTS

| | | | | |
|---|---|---|---|---|
| 9,307,932 | B2* | 4/2016 | Mariani | A61B 5/112 |
| 2005/0010139 | A1* | 1/2005 | Aminian | G06V 40/25 |
| | | | | 600/595 |
| 2008/0146968 | A1* | 6/2008 | Hanawaka | A61B 5/1038 |
| | | | | 600/595 |
| 2012/0092169 | A1* | 4/2012 | Kaiser | A61B 5/6807 |
| | | | | 340/573.1 |
| 2012/0101411 | A1* | 4/2012 | Hausdorff | A61B 5/1117 |
| | | | | 600/595 |
| 2013/0123665 | A1* | 5/2013 | Mariani | A61B 5/6807 |
| | | | | 600/592 |
| 2014/0156215 | A1 | 6/2014 | Eastman et al. | |
| 2014/0303508 | A1 | 10/2014 | Plotnik-Peleg et al. | |
| 2015/0157274 | A1* | 6/2015 | Ghassemzadeh | A61B 5/4082 |
| | | | | 600/595 |
| 2016/0100801 | A1* | 4/2016 | Clark | A61B 5/7278 |
| | | | | 73/865.4 |
| 2016/0107309 | A1* | 4/2016 | Walsh | A61B 5/6831 |
| | | | | 248/550 |

OTHER PUBLICATIONS

M. ElSayed, A. Alsebai, A. Salaheldin, N. El Gayar and M. ElHelw, "Ambient and wearable sensing for gait classification in pervasive healthcare environments," The 12th IEEE International Conference on e-Health Networking, Applications and Services, Lyon, 2010, pp. 240-245 (Year: 2010).*
Gigi R, Haim A, Luger E, Segal G, Melamed E, Beer Y, Nof M, Nyska M, Elbaz A. Deviations in gait metrics in patients with chronic ankle instability: a case control study. J Foot Ankle Res. Jan. 21, 2015;8(1):1. doi: 10.1186/s13047-014-0058-1. PMID: 25653717; PMCID: PMC4316404 (Year: 2015).*
European Search Report regarding corresponding European Patent Application No. 16174268.9, dated Nov. 18, 2016.
International Search Report and Written Opinion regaiding corresponding PCT Application No. PCT/EP2017/064281, dated Sep. 21, 2017.
Yuwono, Mitchell et al., "Unsupervised Segmentation of Heel-Strike IMU Data Using Rapid Cluster Estimation of Wavelet Features," 35$^{th}$ Annual International Conference of the IEEE, Jul. 3, 2013, pp. 953-956.
Communication Pursuant to Article 94(3) EPC regarding corresponding European Patent Application Serial No. 17734647.5, dated Sep. 15, 2021.
Result of Consultation regarding corresponding European Patent Application No. 17734647.5, dated Jun. 27, 2022.
Amboni, Marianna, et al., "Gait Patterns in Parkinsonian Patients With or Without Mild Cognitive Impairment," Movement Disorders, vol. 27, No. 12, 2012, pp. 1536-1543.
Arel, Itamar, et al., "Deep Machine Learning—A New Frontier in Artificial Intelligence Research," IEEE Computational Intelligence Magazine, Nov. 2010, pp. 13-18.
Barth, Jens, et al., "Stride Segmentation during Free Walk Movements Using Multi-Dimensional Subsequence Dynamic Time Warping on Inertial Sensor Data," Sensors, 15, 2015, pp. 6419-6440.
Bishop, Christopher M., "Pattern Recognition and Machine Learning," Springer, 2001, 749 pages.
Burns, Adrian, et al., "SHIMMER—A Wireless Sensor Platform for Noninvasive Biomedical Research," IEEE Sensors Journal, vol. 10, No. 9, Sep. 2010, pp. 1527-1534.
Chen, Xue-Wen, et al., "Big Data Deep Learning: Challenges and Perspectives," IEEE, vol. 2, 2014, pp. 514-525.
Cybenko, G., "Approximation by Superpositions of a Sigmoidal Function," Mathematics of Control, Signals, and Systems, 1989, 2, pp. 303-314.
Day, William, H.E., et al., "Efficient Algorithms for Agglomerative Hierarchical Clustering Methods," Journal of Classification, 1, 1984, pp. 7-24.
Dempster, A. P., et al., "Maximum Likelihood from Incomplete Data via the EM Algorithm," Journal of the Royal Statistical Society, Series B, 1977, pp. 1-38.
Duda, Richard, O., et al., "Pattern Classification—Second Edition," 2000, 671 pages.
Eskofier, B., et al., "Embedded Surface Classification in Digital Sports," Pattern Recognition Letters, 30, 2009, pp. 1448-1456.
Georgescu, Bogdan, et al., "Mean Shift Based Clustering in High Dimensions: A Texture Classification Example," Proceedings of the Ninth IEEE International Conference on Computer Vision, 2003, 8 pages.
Greene, Barry R., et al., "A Comparison of Algorithms for Body-Worn Sensor-Based Spatiotemporal Gait Parameters to the GAITRite Electronic Walkway," Journal of Applied Biomechanics, 28, 2012, pp. 349-355.
Guha, Sudipto, et al., "CURE: An Efficient Clustering Algorithm for Large Databases," ACM SIGMOD Record, vol. 27, Issue 2, 1998, pp. 73-84.
Hollman, John, H., et al., "Number of Strides Required for Reliable Measurements of Pace, Rhythm and Variability Parameters of Gait During Normal and Dual Task Walking in Older Individuals," Gait and Posture, 32, 2010, pp. 23-28.
Horak, Fay B., et al., "Objective Biomarkers of Balance and Gait for Parkinson's Disease Using Body-Worn Sensors," Movement Disorders Official Journal, 28(11), Sep. 15, 2013, pp. 1544-1551.
Jain, A.K., et al., "Data Clustering: A Review," ACM Computing Surveys, vol. 31, No. 3, Sep. 1999, pp. 264-323.
Jarchi, Delaram, et al., "Gait Parameter Estimation From a Miniaturized Ear-Worn Sensor Using Singular Spectrum Analysis and Longest Common Subsequence," IEEE Transactions on Biomedical Engineering, vol. 61, No. 4, Apr. 2014, pp. 1261-1273.
Kanzler, Christoph, M., et al., "Inertial Sensor based and Shoe Size Independent Gait Analysis including Heel and Toe Clearance Estimation," 2015 37th Annual International Conference of the IEEE Engineering in Medicine and Biology Society (EMBC), 2015, pp. 5424-5427.
Klucken, Jochen, et al., "Unbiased and Mobile Gait Analysis Detects Motor Impairment in Parkinson's Disease," PLOS ONE, vol. 8, Issue 2, Feb. 2013, 9 pages.
Lapedes, Alan, et al., "How Neural Nets Work," American Institute of Physics, 1988, pp. 442-456.

(56) References Cited

OTHER PUBLICATIONS

Lord, Sue, et al., "Moving Forward on Gait Measurement: Toward a More Refined Approach," Movement Disorders, vol. 28, No. 11, 2013, pp. 1534-1543.

MacQueen, J., "Some Methods for Classification and Analysis of Multivariate Observations," Proceedings of the Fifth Berkeley Symposium on Mathematical Statistics and Probability, 1967, pp. 281-297.

Mannini, Andrea, et al., "Gait Phase Detection and Discrimination Between Walking-Jogging Activities Using Hidden Markov Models Applied to Foot Motion Data From a Gyroscope," Gait and Posture, 36, 2012, pp. 657-661.

Mariani, Benoit, et al., "3D Gait Assessment in Young and Elderly Subjects Using Foot-Worn Inertial Sensors," Journal of Biomechanics, 43, 2010, pp. 2999-3006.

Mariani, Benoit, et al., "On-Shoe Wearable Sensors for Gait and Turning Assessment of Patients With Parkinson's Disease," IEEE Transactions on Biomedical Engineering, vol. 60, No. 1, Jan. 2013, pp. 155-158.

McDonough, Andrew L., et al.,"The Validity and Reliability of the GAITRite System's Measurements: A Preliminary Evaluation," Arch Phys Med Rehab., 82(3), Mar. 2001, pp. 419-425.

Muro-de-la-Herran, Alvaro, et al., "Gait Analysis Methods: An Overview of Wearable and Non-Wearable Systems, Highlighting Clinical Applications," Sensors, 14, 2014, pp. 3362-3394.

Ngo, Trung Tranh, et al., "Similar Gait Action Recognition Using an Inertal Sensor," Pattern Recognition, 48, 2015, pp. 1289-1301.

Ferraris, Franco, et al., "Procedure for Effortless In-Field Calibration of Three-Axis Rate Gyros and Accelerometers," Sensors and Materials, vol. 7, No. 5, 1995, pp. 311-330.

Perry, J., "Gait Analysis—Normal and Pathological Function," Journal of Physical Therapy Education, vol. 8, No. 1, 1992, 2 pages.

Peruzzi, A., et al., "Estimation of Stride Length in Level Walking Using an Inertial Measurement Unit Attached to the Foot: A Validation of the Zero Velocity Assumption During Stance," Journal of Biomechanics, 44, 2011, pp. 1991-1994.

Rampp, Alexander, et al., "Inertial Sensor-Based Stride Parameter Calculation From Gait Sequences in Geriatric Patients," IEEE Transactions on Biomedical Engineering, vol. 62, No. 4, Apr. 2015, pp. 1089-1097.

Rebula, John R., et al., "Measurement of Foot Placement and its Variability with Inertial Sensors," Gait Posture, 38(4), Sep. 2013, pp. 974-980.

Roiz, Roberta, et al., "Gait Analysis Comparing Parkinson's Disease with Healthy Elderly Subjects," Arquivos de Neuropsiquiatria, 68(1), 2010, pp. 81-86.

Rousseeuw, Peter J., et al., "Silhouettes: A Graphical Aid to the Interpretation and Validation of Cluster Analysis," Journal of Computational and Applied Mathematics, 20, 1987, pp. 53-65.

Roy, S., et al., "An Approach to Find Embedded Clusters Using Density Based Techniques," Dept of Computer Science and Information Technology, 2005, pp. 523-535.

Salarian, Arash, et al., "Gait Assessment in Parkinson's Disease: Toward an Ambulatory System for Long-Term Monitoring," IEEE Transactions on Biomedical Engineering, vol. 51, No. 8, Aug. 2004, pp. 1434-1443.

Shannon, C.E., "A Mathematical Theory of Communication," The Bell System Technical Journal, vol. XXVII, No. 3, Jul. 1948, pp. 379-423.

Skog, Isaac, et al., "Evaluation of Zero-Velocity Detectors for Foot-Mounted Inertial Navigation Systems," 2010 International Conference on Indoor Positioning and Indoor Navigation, Sep. 15-17, 2010, 6 pages.

Trojaniello, Diana, et al., "Estimation of Step-By-Step Spatio-Temporal Parameters of Normal and Impaired Gait Using Shank-Mounted Magneto-Inertial Sensors: Application to Elderly, Hemiparetic, Parkinsonian and Choreic Gait," Journal of NeuroEngineering and Rehabilitation, 11, 152, 2014, 12 pages.

Vieregge, P., et al., "Gait Quantitation in Parkinson's Disease—Locomotor Disability and Correlation to Clinical Rating Scales," Journal of Neural Transmission, 104, 1997, pp. 237-248.

Webster, Kate E., et al., "Validity of the GAITRite Walkway System for the Measurement of Averaged and Individual Step Parameters of Gait," Gait and Posture, 22, 2005, pp. 317-321.

Windolf, Markus, et al., "Systematic Accuracy and Precision Analysis of Video Motion Capturing Systems—Exemplified on the Vicon-460 System," Journal of Biomechanics, 41, 2008, pp. 2776-2780.

Witten, Ian H., et al., "Data Mining—Practical Machine Learning Tools and Techniques—Second Edition," 2005, 558 pages.

Djurić-Jovičić, Milica, et al., "Intra-Subject Stride-to-Stride Variability: Selecting Subject's Representative Gait Pattern," 19th Telecommunications Forum TELFOR 2011, Serbia, Nov. 22-24, 2011, 4 pages.

Extended European Search Report regarding corresponding European Patent Application Serial No. 23151602.2, dated Apr. 12, 2023.

\* cited by examiner

O: toe off; +: heel strike (HS); x: mid stance (MS)

METHOD AND SYSTEM FOR ANALYZING HUMAN GAIT

The present invention relates to methods and systems for analyzing gait of an individual human being.

The ability to move independently is one key factor of human wellbeing and consequently an indicator for quality of life. Thus, movement impairments such as gait impairments lead to a significant loss of independence and quality of life. Major causes of movement impairments, and in particular gait impairments, are diseases such as neurological diseases (e.g. Parkinson's disease), musculo-skeletal diseases or cardio-pulmonal diseases. Similarly, movement impairments often have complex causes which result e.g. from geriatric diseases, trauma, or orthopedic diseases.

In an ageing society, in which movement impairments and causative diseases occur more frequently, an accurate and objective clinical assessment of movement impairments becomes more and more important. Rating the quantity and especially the quality of movements can be a powerful measure for monitoring progression of movement impairments and causal diseases, but also for evaluating the effectiveness of respective treatments. Besides these application areas, movement assessment gains more and more importance in the field of sports, such as for injury process and prevention analysis, performance optimization or product recommendations.

As a distinct movement of the human body, gait is of particular importance for clinical movement assessment, because it is affected by a number of movement-impairing diseases. Accordingly, there is a high interest in clinical gait assessment, such as in monitoring of Parkinson's disease progression (Vieregge et al., 1997, Journal of Neural Transmission 104: pp. 237-248). Clinical assessment of gait is currently in most cases still performed visually by physicians and movement disorder specialists. During state-of-the-art stratified assessments patients typically have to perform predefined gait tests, such as a walk over a defined distance or time. The visual analysis of these tests largely depends on the experience of the physician and is therefore prone to subjective misjudgments and a substantial interrater variability. Moreover, a visual assessment by a physician is time and location dependent and therefore inconvenient for patients. Moreover, given that these tests are typically only performed a few times per year, the risk of misjudgment based on daily fluctuations of the movement impairment is increased considerably.

To improve objective and quantitative gait assessment, a number of electronic measurement systems have been developed (Horak and Mancini, 2013, Movement disorders: official journal of the Movement Disorder Society 28: pp. 1544-51; Mariani et al., 2013, IEEE transactions on biomedical engineering 60: pp. 155-8; Muro-de-la-Herran et al., 2014, Sensors (Basel, Switzerland) 14: pp. 3362-94; Rampp et al., 2014, IEEE Transactions on Biomedical Engineering 62: pp. 1089-1097). These systems allow for acquisition of data from gait sequences of an individual subject. Employing electronic measurement systems and analysis of the acquired data can increase the comparability of gait assessment both on the level of an individual patient and between patients.

One group of electronic measurement systems are stationary gait analysis systems, such as, for example, camera-based optical motion systems or treadmill-based systems (Amboni et al., 2012, Movement disorders: official journal of the Movement Disorder Society 27: pp. 1536-43; Mannini and Sabatini, 2012, Gait & Posture 36: pp. 657-61; Roiz et al., 2010, Arquivos de neuropsiquiatria 68: pp. 81-86). These systems are usually highly precise but can typically only be employed in special environments such as clinics or gait laboratories. Thus, although these systems can increase accuracy of gait assessment, they still underlie the limitations of location dependency and misjudgments due to day-to-day fluctuations of movement ability. Moreover, the use of these systems is currently limited to predefined gait tests rather than diverse movement sequences.

Recently, mobile gait measurement systems relying on inertial sensors, which consist of accelerometers and gyroscopes, have been developed (Mariani et al., 2010, Journal of Biomechanics 43: pp. 2999-3006; Rampp et al., 2014, IEEE Transactions on Biomedical Engineering 62: pp. 1089-1097). These miniaturized sensors can typically be directly attached to clothes and footwear (i.e. the shoes) or the body and are thus ideally suited for mobile movement analysis. Specifically the following sensor systems have been developed and employed for gait analysis:

Mariani et al. developed a system with accelerometers and gyroscopes attached on the instep of a foot to calculate stride features like stride times, stride length, foot angles and clearance (Mariani et al., 2010, Journal of Biomechanics 43: pp. 2999-3006).

A similar approach was used to assess the parameters stride time, stride length, foot angles and clearance in studies of the present inventors. However, in these studies a novel approach for stride segmentation was used, the sensors were attached laterally below the ankle joint and different drift models as well as the methods for gait event detection were employed (Barth et al., 2015, MDPI Sensors 15: pp. 6419-6440; Rampp et al., 2014, IEEE Transactions on Biomedical Engineering 62: pp. 1089-1097).

In another study, Greene et al. used accelerometers and gyroscopes to calculate spatio-temporal stride features during walking. The sensors were attached to the anterior shank and not directly on the foot. This sensor setup/position does not allow to assess foot angles and clearance (Greene et al., 2012, Journal of applied biomechanics 28: pp. 349-55). Trojaniello et al. used also accelerometers and gyroscopes attached to the shank. They chose a position above the ankles. Also with this sensor setup it is not possible to assess foot angles and clearance (Trojaniello et al., 2014, Journal of NeuroEngineering and Rehabilitation 11: pp. 152).

Finally, Rebula et al. developed a system using accelerometers and gyroscopes attached to the heel of the shoe to assess stride-by-stride foot placement and extract information of the stride length and width (Rebula et al., 2013, Gait & Posture 38: pp. 974-980).

However, despite the availability of different mobile sensor systems, mobile gait analysis still has major limitations. In particular, using these systems in daily life is presently difficult, given that the recorded data is highly diverse and represents a number of distinct movements and/or gait events. This diversity of the recorded data typically reduces accuracy of gait analysis as data segments suitable for further analysis are often difficult to identify. Accordingly, in the field of clinical gait assessment, which requires particularly reliable analysis systems, mobile gait analysis systems are currently still limited to stationary settings and defined gait tests, in which the data almost exclusively comprise data representative for gait.

Even though instrumented gait analysis systems are able to obtain data on different strides or gait sequences, one important aspect of instrumented gait assessment has not been solved: It is not clear, how an individual gait profile of a human being can be extracted from a given gait sequence that can be quantified and that is characteristic for either distinct gait impairments (e.g. disease related), or physiological gait patterns (e.g. turning, initiation, stopping, stairway walking, etc.). Nowadays instrumented gait analyses compute stride features from gait sequences by merely calculating the mean of stride features over all (especially in daily life settings often highly heterogenic) strides detected, disregarding the character of individual strides within the gait sequence assessed. Thus, the variability derived from this gait analysis strategy is derived not only from the alterations of the specific gait characteristic (disease related, or physiological gait pattern), but also from individual strides that represent other gait patterns that are not informative for the given gait pattern. For example, if you want to analyze the gait characteristics of a person that is limping and you let this person walk for about 10 meters, several strides represent limping, but might also represent gait initiation, turning, stopping, pausing, etc. Thus, the variation of a 10 meter gait sequence is not only derived from limping, but also from other gait patterns. To overcome this conceptual limit of gait analysis, it has been discussed that a minimum number of strides is necessary to conclude representative gait patterns in order to account for this heterogeneity of strides within a gait sequence (Lord et al., 2013, Movement disorders: official journal of the Movement Disorder Society 28: pp. 1534-43). Currently available standard gait analysis systems typically use a high number of heterogenic strides in order to achieve robust results. (e.g. Hollman et al. suggests more than 300 strides to get reliable results for stride variability) (Hollman et al., 2010, Gait & Posture 32: pp. 23-28). Importantly, however, this approach has still the major limitation that despite a reduced variance the determined stride features are only representative for the most prominent gait pattern in the gait sequence. Reliable stride features with low variance that are representative for rare gait events, as e.g. required for clinical gait assessment, cannot be derived. Furthermore, recording a high number of strides may be a major burden, in particular, for patients having severe movement impairments. Another limitation is that currently available gait analysis do not allow for simultaneously analyze different gait patterns or events comprised in a gait sequence.

Accordingly, there is a high need to overcome the above-mentioned limitations of gait assessment and to provide improved methods and systems for gait analysis from data recorded with electronic measurement systems. This need extends to non-monitored and non-standardized gait sequence analysis such as long term home monitoring, but also standardized gait assessments during supervised laboratory gait analysis. In particular, there is a high need for improved gait analysis systems for gait sequences comprising highly diverse gait events and patterns.

These needs are addressed by the method and system according to the independent claims of the present invention.

The present invention relates to a (computer-implemented) method for analyzing gait of a subject, said method comprising:
a) providing data representing the three-dimensional movement (3D-movement) of a foot of said subject (over time), wherein said 3D-movement comprises a plurality of strides of said foot;
b) identifying within said data first data segments, wherein each of said first data segments represents at least one stride;
c) determining one or more stride features for each of said first data segments; and
d) defining one or more clusters on the basis of at least one stride feature of said one or more stride features, wherein each cluster represents a class of strides.

Furthermore, the present invention also relates to systems for analyzing gait of a subject corresponding to the above-mentioned method.

In particular, the present invention also relates to a system for analyzing gait of a subject, said system comprising:
a) an input for data representing the 3D-movement of a foot of said subject, wherein said 3D-movement comprises a plurality of strides of said foot;
b) one or more processing units adapted and arranged for:
identifying within said data first data segments, wherein each of said first data segments represents at least one stride; and
determining one or more stride features for each of said first data segments; and
defining one or more clusters on the basis of at least one of the one or more determined stride feature(s), wherein each cluster represents a class of strides.

As documented herein below and in the appended example, the methods and systems of the present invention allows for automatic clustering of gait or stride sequences. This allows for improved assessment of unobserved gait/movement sequences, such as non-standardized gait sequence analysis like long term home monitoring, but also standardized gait assessments during supervised laboratory gait analysis. In particular, by grouping the strides into individual clusters with high intra-class homogeneity robust results with a minimum number of strides can be achieved.

As also documented herein below and in the appended example, the method of the present invention allows for identifying strides from movement sequences and subsequently sorting the identified strides in clusters of strides by similarity of one or more stride features. Each of these clusters represents a distinct class/type of strides (e.g. typical strides; strides representing a certain gait impairment etc.). The definition of classes/types of strides with similar stride features provides a number of advantages that improve gait analysis.

A major advantage of the method according to the present invention is that the robust definition of clusters representing classes/types of strides based on one or more stride features allows for selecting only such class/type of strides representative for the type of gait intended to be analyzed. For instance, if the aim is to analyze features of the typical gait of a subject, the cluster representative for the most frequent strides of a gait sequence can be selected by a method of the present invention and taken into account for further analysis. As shown in the appended example, a method according to the present invention could already robustly distinguish from a short movement sequence comprising 206 strides 3 classes/types of strides by clustering based on two stride features. Given that the movement sequence was recorded from a young man, who was walking during the test sequence, it was expected that the typical stride of the walking man will be represented by rather long strides and have low variability. Indeed, the analysis with the method for gait analysis according to the present invention identified a cluster comprising 156 of the strides as the most prominent cluster. As expected the strides from the main cluster are long, have low variability and can therefore be representative for the typical/most frequent stride type and/or typical gait of the test person.

Another advantage is that the method according to the present invention allows for gaining information about the number of different classes/types of strides which are calculated and are present in the data set representing a movement sequence. This has the advantage that a measure about the homogeneity of strides within a movement sequence is provided. Moreover, given that the clustering is performed based on stride features, the method according to the present invention also provides information regarding the features of the identified stride classes/types. This assigns the stride type/class to a stride related to certain movements (e.g. straight walking, running, walking on stairways etc.), which may allow for a more accurate analysis of gait impairments for which said stride features are representative. In the presented example the groups/clusters 2 and 3 represent stairway walking and turning sequences.

Similarly, clustering of strides provides information about how frequently strides with particular stride features arise in a movement sequence. This frequency can, for example, be a measure for the severity of distinct gait impairments that is represented by a defined stride cluster. Thus, the method of the present invention if performed on 3D-movement data recorded over time can be used for detecting certain stride classes/types comprised in complex movement data over time. In other gait analysis methods, which may involve determining average stride features over all strides, these stride classes/types are much more difficult to detect, in particular if they are not prominent.

In the context of the present invention, the term "gait" refers to any kind of walking or running-like movements of a subject. The term gait in particular includes normal walking or running, which is characterized by a number of consecutive strides, preferably at least 2, preferably at least 3, preferably at least 4, preferably at least 5, preferably at least 6, preferably at least 7, preferably at least 8, preferably at least 9 or most preferably at least 10 strides. Similarly, other non-limiting examples for movements included by the term gait in the context of the present invention are up-hill or down-hill walking/running, climbing stairways, jumping, climbing, turning movements, limping.

The term "subject" as used herein refers to a single human being. Thus, the expression "analyzing gait of a subject" means the gait of an individual human being is analyzed. In certain embodiments this may also involve comparing the gait of an individual subject to the gait of other individual subjects. The subject may be a healthy human being, however, it is also particularly envisaged in the context of the present invention that the subject suffers or suffered from impaired motion, preferably impaired gait. In particular, it is envisaged to analyze the gait of a subject that suffers from a disease that impairs motion (and/or impairs gait), preferably a neurological disease, a musculo-skeletal disease and/or a cardio-pulmonal disease and/or a subject suffering from complex causes of movement impairment preferably resulting from geriatric diseases, mono- to polytrauma, monoarticulate orthopedic diseases or systemic orthopedic diseases. A subject may, for example, suffer from a neurological disease selected from the group consisting of Parkinson's disease, Multiple Sclerosis, Huntington's disease, Spastic Paraplegia, Ataxia, Stroke, Dystonia, Chorea, Drug-induced movement disorders, Cerebral Palsy, Pain syndromes, Neuropathies. Moreover, a subject suffering from a complex movement impairment resulting from a geriatric disease may, for example suffer from a disease selected from the group consisting of Sarcopenia and Frailty. It is also envisaged that the gait of a subject suffering from a musculo-skeletal disease, which is, for example, selected from the group consisting of muscle, bone and/or joint Traumata, Myopathy, Myositis, Osteopathy, Osteoporosis, Osteoarthrosis, rheumatological diseases and/or Osteoarthritis.

In the context of the present invention, the term "stride" refers to one gait cycle of the same foot from a subjects' gait. The terms stride and gait cycle can be considered here as synonyms. The "gait" of a subject consists of one or more strides. Start and end events of one stride have to be defined as two identical and consecutive gait events. A gait event that defines start and end of a stride is, for example, heel strike, toe off, mid stance or another distinct event that can be identified during one gait cycle.

In the context of the present invention, the term "data representing the 3D-movement of a foot" means any type of data that contains information about the movement of a foot (and preferably also the corresponding leg) of a subject in the three-dimensional (3D) space over a defined time period. Such data is preferably acquired with an electronic measurement system suitable for detecting movements of a foot in the 3D-space such as sensor-based gait analysis systems. In principle, each measurement system known in the art can be employed. Preferably, sensor systems comprising a 3D-accelerometer and/or a 3D-gyroscope are employed. In other words, preferably a sensor-based measurement system comprising or consisting of a 3D-accelerometer and/or a 3D-gyroscope is employed. The data representing the 3D-movement of a foot, thus, preferably comprises or consists of signals that are obtainable (or obtained) from a 3D-accelerometer and/or a 3D-gyroscope (e.g. mounted on a foot or a worn shoe). In case of a 3D-accelerometer, the data preferably represents the acceleration of a foot in the three-dimensional space described by three axes. The three axes can, for example, be the anterior-posterior movement (subsequently referred to as AX herein), the inferior-superior movement (subsequently referred to as AY herein) and the lateral-medial movement. One or more of the axes may, however, also be used in an inverted manner. Inverted manner means that the axis is rotated by 180°, i.e. the orientation is inverted/opposite. The inverted version of the anterior-posterior movement axis would, for example, be the posterior-anterior movement. The data acquired by a 3D-gyroscope preferably represents the angular rates of three degrees of freedom. These three degrees of freedom are preferably defined as the rotations in the coronal plane around the x-axis (GX), in the transverse plane around the y-axis (GY) and in the sagittal plane around the z-axis (GZ; see FIG. 1b). The x, y, and z axes are in this case defined as described above for the accelerometer data. The direction of the rotation can in principle be chosen in both directions. A preferred example of the directions is shown in FIG. 1b. Illustrative but non-limiting examples for the orientation of the axes that may be used for accelerometer data and gyroscope data are shown in FIGS. 1a and 1b, respectively.

The data representing the 3D-movement of a foot employed in the context of the present invention comprises (or consists of) a plurality of strides of said foot. A plurality of strides, as used herein, in principle, means two or more strides. Preferably, however in the context of the present invention a plurality of strides refers to at least 2, preferably at least 5 strides and most preferably at least 10 strides. The data representing the 3D-movement of a foot employed in the context of the present invention may in addition to strides also comprise data representing other movements of the foot (e.g., heel-toe tapping, circling) and/or time segments in which the foot does not move.

The term "3D-movement" as used in the context of the present invention refers to the movement in the three-dimensional space. In other words, 3D-movement refers to the change of the position in the three-dimensional space over time.

Providing data representing the 3D-movement of a foot, as used herein, includes receiving or retrieving prerecorded data representing the 3D-movement of a foot or measuring such data representing the 3D-movement of a foot. In one aspect, said data may be retrieved from the internet and/or an intranet. The intranet may in particular also include wireless transduction, e.g. via Bluetooth transfer.

In one aspect the data representing the 3D-movement of a foot employed in the context of the present invention may comprise or consist of measuring said data. As mentioned above, the data can, in principle, be measured by any kind of measurement system that allows measuring the 3D-movement of a foot (and preferably leg). Examples are optical motion tracking systems like Bonita Motion Capture (Vicon Motion Systems, Oxford, United Kingdom), OptiTrack (NaturalPoint, Corvallis, United States) and Qualisys (Qualisys AB, Göteborg, Sweden). Preferably, measuring involves using a 3D-accelerometer and/or a 3D-gyroscope. In particular, it is envisaged to employ a sensor system comprising (or consisting of) a 3D-accelerometer and/or a 3D-gyroscope. Non-limiting examples for such sensor system are x-IMU (x-io Technologies, Bristol, United Kingdom), Physiolog Motion Sensor (Gait Up SA, Lausanne, Switzerland) or MTw wireless motion trackers (Xsense, Enschede, The Netherlands). In particular, as illustrated by the appended examples, a sensor system, referred to as eGaIT system may be employed (Kanzler et al., 2015, 2015 37th Annual International Conference of the IEEE Engineering in Medicine and Biology Society (EMBC) pp. 5424-5427). The eGaIT system is an inertial sensor measurement system, which consists of a sensor unit which is attached on the lateral side of a shoe (see FIG. 1). Optionally, if 3D-movement of a subject is monitored, the eGaIT system may comprise two sensor units attached a pair of shoes, wherein one sensor unit is attached on the lateral side of each of the two shoes. A sensor unit, which can be employed in the context of the present invention and in particular in the context of the eGaIT system, is the Shimmer 3® sensor unit that was developed by Shimmer sensing (Dublin, Ireland). The Shimmer 3® sensor unit includes a tri-axial (3D) gyroscope (InvenSense MPU9150, range of ±1000°/s, sensitivity of 16LSB/°s) and a tri-axial (3D) accelerometer (STMicroelectronics, LSM303DLHC, range of ±8 g, sensitivity of 83LSB/g) (Burns et al., 2010, IEEE Sensors Journal 10: pp. 1527-1534). The Shimmer 3® sensor unit data can, for example be recorded wirelessly via Bluetooth with a sampling rate of up to 1024 Hz.

In the context of the present invention in particular measurement systems comprising (a) sensor unit(s) that are attached to the foot or preferably the shoe worn by a subject may be employed. The positioning of such sensor units on the foot and/or shoe of a subject, is preferably on the lateral side of a foot or preferably a shoe worn by said subject (e.g. on a respective position of the shoe surface, preferably as shown in FIG. 1). Particularly preferred is a position below the ankle joint of the subject. As described by Peruzzi et al., such a sensor position is particularly well suited for determining distinct spatio-temporal stride features from the measured data (Peruzzi et al., 2011, Journal of Biomechanics 44: pp. 1991-1994). Thus, this sensor position is particularly well-suited for providing data suitable for a method for gait analysis according to the present invention.

Depending on the format of the data representing the 3D-movement of a foot of a subject, providing the data may further comprise a preprocessing step after receiving or measuring the data. Preprocessing may, for example, include alignment of one or more sensor axes and/or transformation/conversion of the recorded raw sensor signal. Axes alignment means that the orientation of the axis used to depict 3D-movement data may be aligned to a set of predefined axes. Axes alignment may in particular be employed if the 3D-movement of both feet of a subject is analyzed simultaneously. In such case axes alignment may be performed in a way that strides with both feet are comparable. For example, as illustrated in the appended examples, inversion of certain axes can be required for axes alignment. For a sensor setup and positioning as used in the appended example (see FIG. 1), for example, the orientation of the left sensor unit may be taken directly from the hardware and is defined by the axes (and axes orientations) as described in FIG. 1. Due to opposite sensor unit mounting on the right shoe in this particular example, axes of the right sensor unit may be inverted to get comparable signals and to maintain the algebraic sign of the data (compared to the left sensor). In such scenario, in particular, the AX: anterior-posterior movement; GY: angular rate in transverse plane and GZ: angular rate in sagittal plane axis of the right sensor may be inverted. Alternatively also the data of the right sensor could be used unmodified and the respective data axes of the left foot may be inverted. Axes alignment may also be performed if data recorded with different measurement systems that have different measurement axes is analyzed in the context of the present invention.

Should the received or measured data not be depicted in the unit intended to be retrieved by the respective sensor (e.g. $m/s^2$ for accelerometer data or °/s for gyroscope data), the step of providing the data may further comprise conversion of the raw sensor data (typically given in mV) to the actual unit(s) intended to be measured by a sensor. The conversion of the raw sensor signal can be achieved by methods known in the art (Parvis and Ferraris, 1995, Sensors and Materials 7: pp. 311-330). In principle, these methods use calibration data sets with defined movements that allow defining the mapping to the respective units. To convert raw accelerometer data (given in mV) into the unit $m/s^2$ and/or raw gyroscope data (given in mV) into °/s, a method described by Ferraris and coworkers (Parvis and Ferraris, 1995, Sensors and Materials 7: pp. 311-330) can, for example, be employed. In brief, the sensor raw data calibration described by Ferraris and coworkers consists of the determination of the bias, scale factor and orientation of the sensors. To determine these factors only a set of standardized rotations and static measurements need to be performed. The bias is a simple additive constant for each axis of accelerometer or gyroscope. Depending on the sensor range the scaling matrix is needed to scale the raw outputs to the usually used units. With the measured orientation the impact of the linear acceleration on the gyroscope sensor output can be corrected. To record calibration files for the method of Ferraris and coworkers, static measurements on each side of the sensor and 360° rotations around the three axes have to be performed. In the context of the method of the present invention (first) data segments representing at least one or more strides are identified within data representing the 3D-movement of a foot.

The term "data segment", as used herein refers to a section/segment of the data representing the 3D-movement of a foot of a subject. The start and end points of the segment/section are preferably defined by the starting and end time of the respective section/segment. The data comprised in a data segment can be one data curve representing the corresponding time section/segment (e.g. a certain axes of the acceleration data and/or a certain rotation plane of the gyroscope data), but can also comprise several and/or all of the data curves representing the corresponding time section/segment (e.g. data curves of different axes and/or sensors describing the 3D-movement of a foot). Thus, if the 3D-movement data of the foot is recorded with a sensor system comprising a 3D-gyroscope and/or a 3D-accelerometer, a data segment may include the data of one, several and/or all six axes/degrees of freedom of the respective data.

The step of identifying within data representing the 3D-movement of a foot over time data segments that represent at least one stride in other words means that within the 3D-movement data respective data sections corresponding to one or more strides are defined (this step is referred to as stride identification). Identifying such data segments in particular includes defining the two time points on the time axis, i.e. the beginning and end of the segment (e.g. a stride), thereby defining said data segments. Identifying data segments each representative for one or more strides within such data may also include identifying within the 3D-movement of a foot over time (e.g. data that comprises several distinct movements of a foot) the relevant information representing strides. The relevant information may be characteristic data points or data segments representing a stride. Accordingly, the step of identifying first data segments that each represent at least one stride (preferably at most 2 consecutive strides) within the 3D-movement data of a foot may be or may involve: (i) identifying strides in the 3D-movement data of a foot provided in a); (ii) defining first data segments each representing one or a sequence of consecutive strides (preferably at most two consecutive strides, e.g. 1, 1.5 or 2) of the strides identified in (i). In other words, stride identification may involve (i) identifying data/data segments representing one stride or a sequence of consecutive strides (preferably at most 2 consecutive strides, e.g. 1, 1.5 or 2) within the 3D-movement data of a foot provided in a); and (ii) defining first data segments representing at least one stride (preferably at most two consecutive strides, e.g. 1, 1.5 or 2 consecutive strides), wherein the start and end position/time of the first data segments may or may not be different from the data segments identified in (i). Preferably, at least 10%, preferably at least 20%, more preferably at least 30%, even more preferably at least 40%, even more preferably at least 50%, even more preferably at least 60%, even more preferably at least 70%, even more preferably at least 80%, even more preferably at least 90% and most preferably all of the strides/data representing strides identified in (i) of the process of identifying of first data segments are covered by the first data segments defined in step (ii). Steps (i) and (ii) of stride identification process may be performed as a single step or as two separate steps. Step (ii) of the process of stride identification may comprise determining one or more stride events within the stride data/data segment. Said one or more stride events are preferably selected from the group consisting of: heel-strike (HS), mid-stance (MS) and toe-off (TO). Methods to identify these stride events are well-known in the art and are described elsewhere herein, e.g., in the appended examples. Further, step (ii) may comprise defining first data segments each representing one or more strides taking into account the one or more defined stride events of a stride or consecutive strides (e.g. two consecutive strides). For instance, first data segments that each comprise certain types and/or numbers of stride events, preferably in a defined order may be defined. Such preferred first data segments are defined in detail further below. Preferred first data segments may be first data segments each comprising at least two consecutive heel-strike events two consecutive midstance events and one toe-off event. Particularly preferred are first data segments that comprise exactly two consecutive heel-strike events exactly two consecutive midstance events and exactly one toe-off event. Such first data segments are ideally suited to calculate different stride features. Preferably, the order of the stride events comprised in each of the first data segments is consecutive as expected in a stride cycle (see, e.g. FIG. 6B). Even more preferably the first gait event within each of the first data segments is a heel-strike. Most preferably, the order of the (exactly) two consecutive heel-strike events, the (exactly) two consecutive midstance events and the (exactly) one toe-off event comprised in each of the first data segments may be HS-MS-TO-HS-MS in each of the first data segments. In other words, a first data segment may comprise the number and order of gait events as shown in FIG. 6B. It is also envisaged that each of the first data segments may start with a heel-strike event and end with the second consecutive mid-stance event following said heel-strike event.

The first data segments may be defined in a manner that per stride identified in step i) of the identification of said first data segments only one first data segment is assigned. Alternatively, also more than one first data segments may be assigned per stride. In other words, two or more of the first data segments may be indexed to a single stride identified in i). In this event, also the stride features defined on the two or more indexed first data segments may be assigned to the stride they are assigned to. Then also the clustering of the strides may be based on stride features that have been derived from more than one of the data segments assigned to a single stride.

Stride identification can, in principle, be performed manually, but is preferably performed automated (computer-implemented). Also combinations of manual and automated stride identification can be used in the context of the present invention. Independent of manual or automated implementation, stride identification may comprise comparing said data with a predefined data set. Said predefined data set may in particular be a data segment representing at least one, or preferably one stride. In one embodiment said predefined data set may be adapted to a type of impaired motion, preferably gait (e.g. gait impairments caused by any of the diseases mentioned herein, preferably Parkinson's disease). Similarly, a predefined data set may also be adapted to the subject who's gait is intended to be analyzed, i.e. may be an individualized predefined data set. A predefined data set may in the context of stride identification, in particular, be a data segment representing a characteristic stride or sequence of (consecutive) strides (preferably 1.5 or 2 consecutive strides) of one or more subjects (e.g. one or more subjects suffering from a motion impairing disease (see elsewhere herein) and/or the subject who's gait is intended to be analyzed). A data segment representing a characteristic stride or sequence of (consecutive) strides can, for example, be determined by calculating the average of several (at least 2, preferably 5, more preferably at least 10) data segments representing a characteristic stride or sequence of (consecutive) strides, respectively.

Manual stride identification by a skilled person may, for example, rely on the pre-knowledge of the typical shape of a data curve that corresponds to a stride. Such pre-knowledge can, for example, be gained by observing the data recorded with the same measurement system during a predefined gait sequence of one or more subject(s). In the context of the present invention the step of identifying strides is preferably achieved by an automated process, e.g. a computer-implemented process. The automated identification of strides often also referred to as stride segmentation herein and elsewhere, can be achieved by methods known in the art. For example, one of the methods described in any of the following references may be employed: (Barth et al., 2015, MDPI Sensors 15: pp. 6419-6440; Mannini and Sabatini, 2012, Gait & Posture 36: pp. 657-61; Ngo et al., 2015, Pattern Recognition 48: pp. 1289-1301; Salarian et al., 2004, IEEE Transactions on Biomedical Engineering 51: pp. 1434-1443). In the context of the present invention, stride identification or segmentation is preferably achieved by (or preferably involves) using an algorithm comprising a Hidden Markov Model for stride segmentation (Mannini and Sabatini, 2012, Gait & Posture 36: pp. 657-61), a Robust event detection (Ngo et al., 2015, Pattern Recognition 48: pp. 1289-1301), a Subsequence Dynamic Time Warping (Barth et al., 2015, MDPI Sensors 15: pp. 6419-6440), a Conditional Random Field Algorithm, a Longest Common Subsequence Algorithm (Jarchi et al., 2014, IEEE Transactions on Biomedical Engineering 61: pp. 1261-1273), a Deep learning algorithm and/or a Threshold (Salarian et al., 2004, IEEE Transactions on Biomedical Engineering 51: pp. 1434-1443) or Matched Filter/Cross-correlation. The algorithms are listed by preference in the context of the present invention; i.e. the first mentioned (a Hidden Markov Model for stride segmentation) is used most preferably, the last mentioned (Threshold or Matched Filter/Cross-correlation) is used least preferred (Bishop, 2001, pp; Duda et al., 2000, pp.). All the above listed algorithms are well known in the art and those skilled in the art know how to implement these algorithms for stride identification.

The basic principle underlying the stride identification by the above-mentioned algorithms is that they compare the data representing 3D-movement of a foot with a predefined data set. Said predefined data set may be a characteristic data segment that is intended to be identified, i.e. a data segment representing at least one (preferably at least one and at most 2 strides) that preferably originates from the same measurement system as used for recording the 3D-movement data of a foot. In particular the predefined data set may have the same or essentially the same starting and end points as the first data segments intended to be identified. Alternatively, the predefined data set may be a data segment representative for a stride, stride sequence or a part of a stride with different start and end than the data segment intended to be identified. In the latter scenario, comparing the 3D-movement of a foot with predefined data may be, or may be a part of, step i) of identifying first data segments each of which represents at least one stride. The characteristic data segment may have the same segment length and/or segment start and/or end positions as the first data segments intended to be identified. Alternatively, in particular when the above mentioned identification of first data segments comprising i) and ii) as mentioned above is employed the data segment used as characteristic segment/template may also have a different length and/or a different start and/or end position than the first data segments that are intended to be identified/defined. The predefined data set may also be adapted to a type of impaired motion, preferably gait (e.g. gait impairments caused by any of the diseases mentioned herein, preferably Parkinson's disease). Similarly, a predefined data set may also be adapted to the subject who's gait is intended to be analyzed. A predefined data set may in the context of stride identification, in particular, be a data segment representing a characteristic stride or sequence of consecutive strides (preferably 1.5 or 2 strides) of one or more subjects (e.g. one or more subjects suffering from a motion impairing disease (see elsewhere herein) and/or the subject who's gait is intended to be analyzed). A data segment representing a characteristic stride or sequence of consecutive strides (a template data segment) can, for example, be determined by calculating the average of several (at least 2, preferably 5, more preferably at least 10) data segments representing a characteristic stride or sequence of consecutive strides. Such templates can then be used in an algorithm-specific manner, which is well known to the person skilled in the art, for identifying data segments representing one or a sequence of consecutive strides. The data segments representing one or a sequence of consecutive strides resulting from stride identification are also referred to as first data segments herein. Each of the identified (first) data segments represents preferably at most three consecutive, preferably at most two consecutive strides. In particular, it is also envisaged that each (first) data segment (resulting from stride segmentation) represents at least 1.5 strides. This is in particular the case if stride feature determination (see further below) is achieved from different (i.e. more than one) data segments that are assigned to the same stride. Preferably, the (first) data segment(s) (resulting from stride segmentation) represent two (consecutive) strides or not more than two (consecutive) strides. In one preferred embodiment, the identified (first) data segments may also represent one stride. Preferably each of the identified (first) data segments comprises at least two consecutive heel-strike events and/or (preferably and) at least two consecutive mid-stance events. It is particularly preferred that each of the first data segments comprises at most two consecutive heel-strike events and/or (preferably and) two consecutive mid-stance events. Accordingly, it is preferred that each of the first data segments comprises at least two consecutive heel-strike events and/or (preferably and) at least two consecutive mid-stance events and at most two consecutive heel-strike events and/or (preferably and) at most two consecutive mid-stance events. Further, it is preferred that the data segment comprises at least one (e.g. exactly one or two), preferably exactly one toe-off event. Said toe-off event is preferably a toe-off event between the consecutive heel-strike and consecutive mid-stance events. Accordingly, each of the first data segments may comprise at least and/or at most the data segments comprising a series of consecutive stride events in the order HS-MS-TO-HS-MS. Accordingly, the first data segments may be data segments that are each representative for at least one stride and at most two strides and that comprise two consecutive heel strike events and/or two consecutive mid-stance events. Methods how to identify and define gait events such as heel-strike events, mid-stance events or toe-off events are in data/data segments are described elsewhere herein and may be employed when the data segments are identified, e.g. in step (ii) of a two step stride identification. Particularly preferred is furthermore that all first data segments represent the same number of strides. It is also envisaged that all first data segments start and end with the same respective gait event(s) or characteristic data points of a stride cycle data. An illustrative but non-limiting example of how stride segmentation can be performed is explained in detail in the appended examples. It is important to note that the first data segments defined in the context of the present invention are preferably physiologically relevant data segments, i.e. they are not just random time segments but are preferably defined to contain a certain number of strides or stride events (see above), which makes them representative for strides and allows precise determination of stride features. In other words, the defined first stride segments are preferably designed to be physiological relevant, i.e. are defined to be data segments that each represent a stride or a sequence of consecutive strides (e.g. two strides). It is particularly preferred that the identified first data segments represent one or at most two consecutive strides. This allows to determine stride feature (s) and to subsequently cluster strides or the data segments comprising at most two consecutive strides by taking into account the determined stride feature(s). A stride may in this context in particular be represented by a mid stance to mid stance event or a heel strike to heel strike event. However, any other definition can also be used. In particular, also a definition based on the respective data type may be used. For example, in the context of using a gyroscope, a stride may also be defined by defining its start and end by two consecutive negative peaks in the sagittal plane angular rate data axis (GZ).

In the context of the present invention, in particular, for example, in the context of the method for analyzing gait of a subject according to the present invention (step c), one or more stride features are determined for strides and/or any of the (first) data segments representing at least one stride. Preferably at least two, or preferably at least three stride features are determined. In the context of the present invention, the term "stride feature" means properties or characteristics of a stride. These properties can be based on any information comprised in a data segment(s) which is/are representing a stride. Stride features according to the present invention include in particular any stride features known in the art and as, for example, described in any of the following publications: (Eskofier et al., 2009, Pattern Recognition Letters 30: pp. 1448-1456; Klucken et al., 2013, PLoS ONE 8: pp. e56956; Rampp et al., 2014, IEEE Transactions on Biomedical Engineering 62: pp. 1089-1097). In particular, the term stride features includes biomechanical and generic stride features (Eskofier et al., 2009, Pattern Recognition Letters 30: pp. 1448-1456; Klucken et al., 2013, PLoS ONE 8: pp. e56956). Thus, the determined stride features preferably are or comprise biomechanical stride features and/or generic features. The biomechanical stride features (Rampp et al., 2014, IEEE Transactions on Biomedical Engineering 62: pp. 1089-1097) are preferably selected from the group consisting of stride time, stride length, swing time, stance time, angle course, angle heel-strike, angle toe-off, clearance course, maximum toe clearance, minimum toe clearance, cadence, stride velocity, ground turning angle, medio-lateral sway, double support time and heel clearance course. The generic stride features are preferably selected from the group consisting of entropy, mean value, variance, root mean square, minimum, maximum, kurtosis, skewness, dominant frequency, energy in frequency band 0.5 to 3 Hz, energy in frequency band 3 to 8 Hz, energy ratio, signal energy.

"Biomechanical stride features" are physically-describable stride parameters (Perry, 1992, Normal and pathological function 1: pp.). Preferably such biomechanical stride features are spatio-temporal stride features; i.e. stride features describing features of the strides referring to space and time. The biomechanical stride features thus preferably include temporal stride features and spatial stride features. Accordingly, the one or more stride features determined in the context of the method according to the present invention may also be or comprise spatial stride feature(s). Similarly, the one or more stride features determined in the context of the method according to the present invention may also be or comprise temporal stride feature(s). Preferred but non limiting temporal stride features that may be determined/employed in the context of the present invention, in particular in step c) of the method according to the present invention, are stride time, swing time and/or stance time. Preferred but non limiting spatial stride features that may be determined/employed in the context of the present invention, in particular in step c) of the method according to the present invention, are the heel strike angle, the toe off angle, and/or stride length.

In the following the stride features that may be determined (and employed for clustering) are defined. Non-limiting examples how these stride features can be determined from the data segments representing at least one stride are given below.

Definitions Temporal Stride Features:

Stride time, which is the time interval in seconds between two consecutive heel strike events, e.g. heel strikes, of the same foot. It can, for example, be calculated with the following formula:

$$d_{stride} = \frac{t_{HS}(i+1) - t_{HS}(i)}{f_s}$$

Swing time, which is defined as the time interval between toe off and heel strike of the same foot. This time interval equals the swing phase, i.e. the interval when the foot is in the air and has no ground contact. It can, for example, be determined with the following formula:

$$d_{swing} = \frac{t_{HS}(i) - t_{TO}(i)}{f_s}$$

Complementary to swing time, stance time is the time interval when the foot is on the ground. Stance time starts with heel strike and ends with toe off. Stance time can, for example be determined as follows:

$$d_{stance} = \frac{t_{TO}(i+1) - t_{HS}(i)}{f_s}$$

In any of the formulas mentioned herein $t_{TO}(i)$, $t_{HS}(i)$ and $t_{MS}(i)$ means functions which model the definition of the stride events toe off (TO), heel-strike (HS) and mid stance (MS) respectively. These functions deliver the point in time within data segment/stride i, where the event occurred. Due to the discrete signal processing, time points t(i) represent sampling values instead of absolute time. To get the results in seconds (duration d), each temporal parameter has to be scaled with the sampling frequency $f_s$.

Definitions Spatial Stride Features

Angle course is the angle between foot and ground in the sagittal plane during one stride. The angle course is measured in degree. It can, for example, be calculated as described in Rampp et al. (Rampp et al., 2014, IEEE Transactions on Biomedical Engineering 62: pp. 1089-1097). For example, first of all the complete angle course of one stride may be determined by estimating the initial angle from e.g. accelerometer data on the mid stance event. Then, e.g. with the angular rate data of the gyroscope and the initial angle the complete angle course of the stride cycle can be calculated. In the example of Rampp et al. the angle course starts and ends at mid stance events.

The heel-strike angle is the angle between foot and ground in the sagittal plane at heel strike event. The angle at heel-strike event can, for example be taken from the stride angle course as it is described in Rampp et al. (Rampp et al., 2014, IEEE Transactions on Biomedical Engineering 62: pp. 1089-1097).

The toe-off angle is the angle between foot and ground in the sagittal plane at toe off. The angle at toe off event can, for example be taken from the stride angle course as it is described in Rampp et al. (Rampp et al., 2014, IEEE Transactions on Biomedical Engineering 62: pp. 1089-1097).

Stride length is the distance in cm between two consecutive mid stance events. It can be calculated with the formulas described in Rampp et al. (Rampp et al., 2014, IEEE Transactions on Biomedical Engineering 62: pp. 1089-1097): Based on the information of the stride angle during the gait cycle and the accelerometer sensor data, the acceleration may, for example, be integrated twice to calculate the covered distance from one mid stance event to the next.

The toe clearance course is the distance in cm between toe and ground during swing phase. It can, for example, be calculated as described in Kanzler et al. (Kanzler et al., 2015, 2015 37th Annual International Conference of the IEEE Engineering in Medicine and Biology Society (EMBC) pp. 5424-5427). To calculate the toe clearance, the sensor clearance can, for example, be calculated by integrating the acceleration signal twice like it is described above. With the help of trigonometric functions and the angle at toe off event, the distance between sensor and toes can be estimated. The sensor-toe distance again can be subtracted or added from the sensor clearance dependent on the foot angle with the help of trigonometric functions to calculate the toe clearance. Similar to the angle course the clearance course is also calculated from mid stance to mid stance event.

The maximum toe clearance is the maximum of the toe clearance. The distance in cm between toe and ground during swing phase is defined as toe clearance.

The minimum toe clearance is the minimum of the toe clearance during swing phase. The distance in cm between toe and ground during swing phase is defined as toe clearance.

The heel clearance course is the distance in cm between heel and ground during swing phase. It can, for example, be calculated as described in Kanzler et al. (Kanzler et al., 2015, 2015 37th Annual International Conference of the IEEE Engineering in Medicine and Biology Society (EMBC) pp. 5424-5427). To calculate the heel clearance, the sensor clearance can, for example, be calculated by integrating the acceleration signal twice like it is described above. With the help of trigonometric functions and the angle at heel strike event, the distance between sensor and heel can be estimated. The sensor-heel distance again can be subtracted or added from the sensor clearance dependent on the foot angle with the help of trigonometric functions to calculate the heel clearance. Similar to the angle course the clearance course is also calculated from mid stance to mid stance event.

The double support time is the time where both feet simultaneously have ground contact and can be calculated from the overlapping stance times. The double support time requires a synchronized signal recording from both feet.

The ground turning angle is the angle change in the transverse plane over one stride. The ground turning angle is measured in degree and is calculated from mid stance to mid stance. It represents the angle change of one stance phase to the following and describes the turning of one foot over one stride. The calculation of the ground turning angle can be done by integration of the angular velocity analogue to the computation of angle course.

The medio-lateral sway is the maximal deviation perpendicular to the forward movement of the foot during swing phase of one stride from one stance phase to the next stance phase. The sway can be given in cm and can, for example, be calculated by integration of angular rate and acceleration of one foot twice analogue to the computation of stride length.

Definitions of Generic Stride Features:

The generic stride features can in principle be calculated from arbitrary data segments and sensor signals. In the 3D gait analysis with accelerometers and gyroscopes, for example, each generic feature is calculated for each of the three axes of accelerometer and each off the three axes of gyroscope data individually. The start and end definition of the data segment to calculate generic stride features is also arbitrary, but have to be consistent in one data analysis procedure. Preferably the definition of the stride to calculate the generic stride features is similar to previous used definition, like for example, by two consecutive negative peaks in the sagittal plane angular velocity data axis (GZ) the stride is, for example, the direct output from the stride segmentation algorithm.

Entropy of a discrete (preprocessed) sensor signal of a data segment representing at least one stride X, is a measure of uncertainty. The content of information is maximal if all events occur with the same probability. A histogram can, for example, be used to get the probability P for one event $x_i$. Information content is defined as $$I(P(x_i)) = -\log_2 P(x_i)$$

The entropy H is the mathematical expectation of information content (Shannon, 1948, MD computing computers in medical practice 27: pp. 306-17):

$$H(X) = -\sum_i P(x_i) \log_2 P(x_i)$$

The mean value of a series of values (e.g. the signal of a data segment). The mean value $\mu$ can, for example, be calculated by determining the mean of all data points of the data segment (as defined by a starting time and end time) representing a respective stride. In particular, the mean value can, for example, be determined as follows:

$$\mu = \frac{1}{n}\sum_i x_i$$

The variance is a measure for the spread of the signals within the data segment representing at least one stride. It can, for example, be calculated as follows:

$$\sigma^2 = \mathrm{Var}(X) = \sum_i P(x_i)(x_i - \mu)^2$$

The Root Mean Squared (RMS) is defined as the square root of the square of the signals within the data segment representing at least one stride. It can, for example, be calculated with the following formula:

$$RMS(X) = \sqrt{\frac{1}{n}\sum_i x_i^2}$$

The minimum of the signal is the lowest value apparent in the signal of a data segment representing at least one stride.

The maximum of the signal is the highest value apparent in the sensor signal of a data segment representing at least one stride.

Kurtosis describes the shape of the sensor signal of a data segment representing at least one stride, e.g. how peaky the signal is. It is the fourth standardized moment. Kurtosis is defined as:

$$Kurtosis(X) = \frac{E(X-\mu)^4}{\sigma^4}$$

where X is the data segment (e.g. a stride), E is the expectation value, μ is the mean value and σ is the standard deviation.

Skewness describes the asymmetry of the sensor signal of a data segment representing at least one stride around the mean. It is the third standardized moment. It is calculated using following formula:

$$Skewness(X) = \frac{E(X-\mu)^3}{\sigma^3}$$

where X is the data segment (e.g. a stride), E is the expectation value, μ is the mean value and σ is the standard deviation.

Signal energy is the sum of the absolute values of the Fourier-transformed (preprocessed) sensor signal of a data segment representing at least one stride between 0 and 50 Hz. Parts above 50 Hz are considered as noise when analyzing motion data.

The dominant frequency of the (preprocessed) sensor signal of a data segment representing at least one stride is defined as the index of the maximum value in the Fourier transformed signal. It characterizes the main speed during tests.

The energy ratio is the complete sequence energy of the (preprocessed) sensor signal of a data segment representing at least one stride divided by the energy value of the dominant frequency.

The energy in a frequency band describes parts of distinct frequencies in the (preprocessed) sensor signal of a data segment representing at least one stride; typical frequency bands for specific movements can be defined. It is, for example determined by building the sum of the absolute values of the Fourier transformed signal between the two frequencies. Preferably, the energy of the frequency band between 0.5 Hz and 3 Hz is determined. In the frequency band 0.5 Hz to 3 Hz most of the common movements in gait tests appear.

Moreover, the energy of the frequency band between 3 Hz and 8 Hz can be determined. The energy in a frequency band 3 Hz to 8 Hz is calculated as the energy in the frequency band above. If, for example, the gait of a person suffering from Parkinson's disease, the frequency band 3 Hz to 8 Hz is typically representing this tremor.

Determining one or more stride features may comprise definition of stride events (distinct events during a stride), preferably selected from the group consisting of heel strike, toe off and mid stance (as also evident from the above mentioned definitions referring to these terms). The heel strike, toe off and mid stance events of strides can, for example, be determined as described by Rampp and coworkers (Rampp et al., 2014, IEEE Transactions on Biomedical Engineering 62: pp. 1089-1097). The appended examples briefly summarize the method employed by Rampp and coworkers.

Figure 6A:
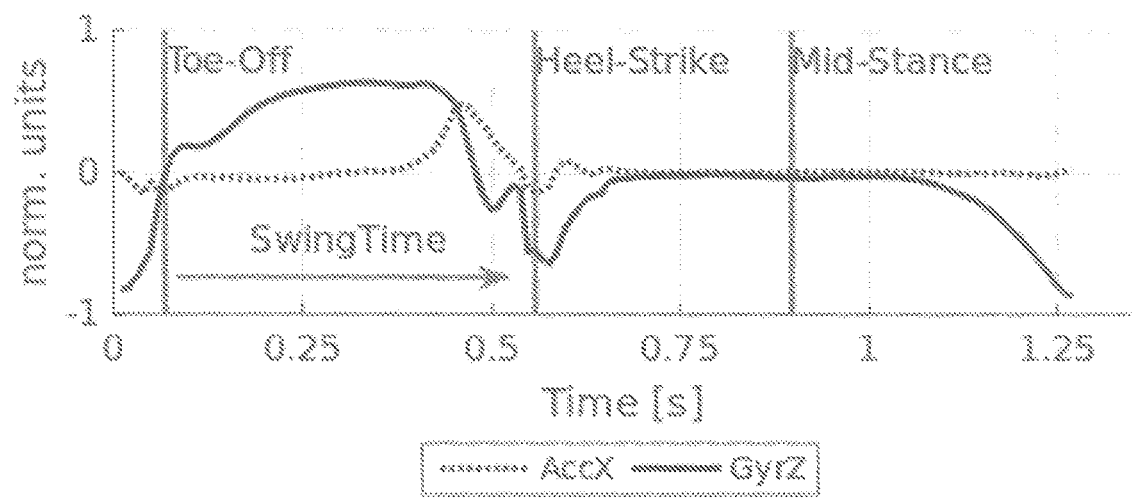
Figure 6B:
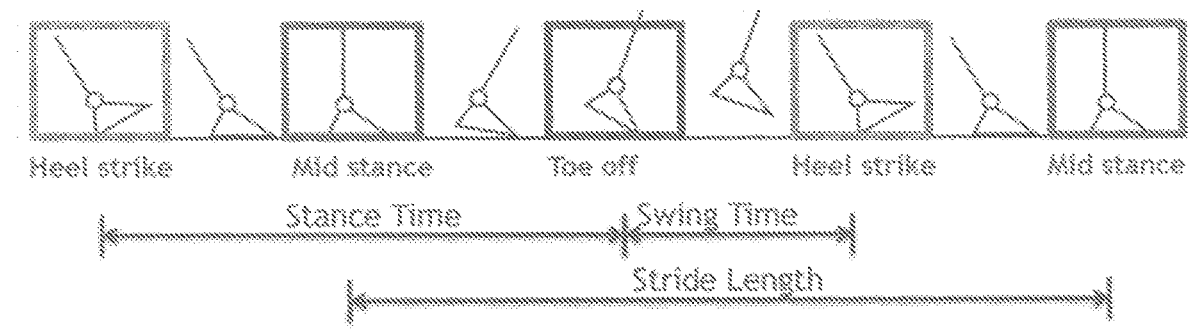

FIG. 6a exemplifies the definition of the toe off, mid stance and heel strike event based on one data segment gained by stride segmentation. The toe off event is defined as the event of a stride at which the toes leave the ground. The mid stance event is defined as the event of a stride when the full foot is on the ground. The heel strike event is defined as the event of a stride when the heel touches the ground. These definitions are schematically illustrated in FIG. 6b.

Figure 7:
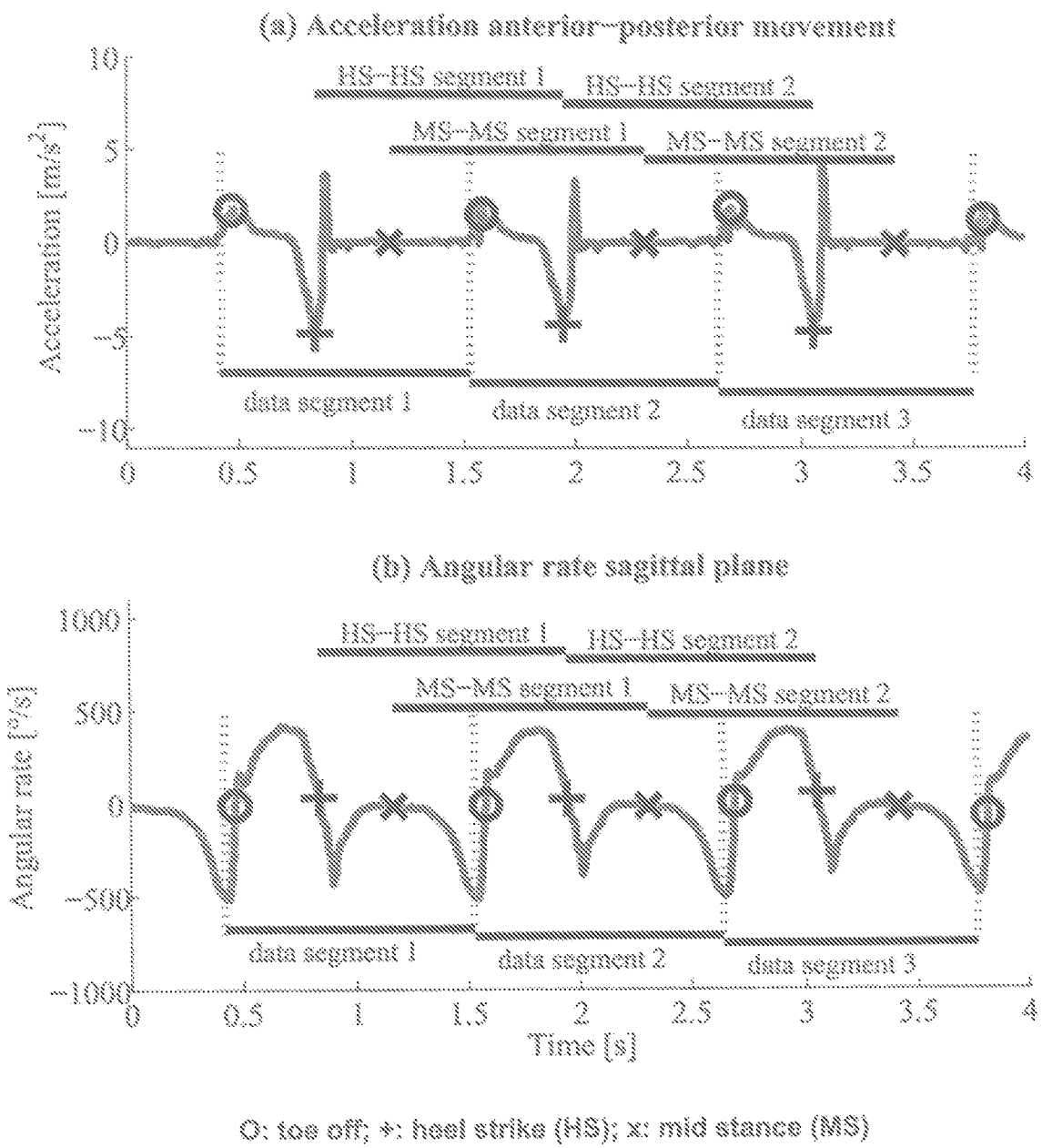

The definition of the above-mentioned stride events may also be used for determining for each of the selected strides next to the initially identified first data segment (during stride segmentation) further data segments representing the same. In particular, a data segment in which the start and the end point are defined by two consecutive heel strike events (HS-HS segment) or two consecutive mid stance events (MS-MS segment) may be defined for each stride. These further data segments may then be used for calculating the one or more stride features. FIG. 7 exemplary illustrates how the respective data segments are defined and assigned to the respective strides. The additional data segments (the HS-HS segment and the MS-MS segments) representing the strides have the advantage of being particularly well suited for determining a variety of distinct stride features (in particular biomechanical stride features).

As mentioned above, the first data segment may comprise stride sequences (i.e. two or more consecutive strides). In this event, determining one or more stride features for each of said first data segments may comprise defining one or more sub-data fragments representing that are assigned to each of the strides in this stride sequence of a first data segment. Subsequently, stride features for each of the strides of the stride sequence of a first data segment may be determined. Optionally, one or more average stride features assigned to a respective first data segment may be determined for each of the first data segments comprising a stride sequence. For the subsequent clustering (e.g. of the first data segments) the stride features of the individual strides of a stride sequence of a first data segment and/or the average stride features of the strides comprised in the first data segment may be used.

The stride features for a stride or a data segment representing at least one stride may be determined as described above and in the examples of the present invention (in particular e.g. in step c) of the method of the present invention). Alternatively, in one embodiment of the present invention determining at least one of said one or more stride features (in particular in step c) may involve or be achieved by a machine learning algorithm. In one embodiment also all of the one or more stride features determined in step c) may be determined by a machine learning algorithm. Preferably a machine learning algorithm selected from the group consisting of Deep Neural Network, Deep Convolutional Neural Networks, Deep Belief Network, Convolutional Deep Belief Network and Multilayer-Kernel-Machines may be employed in the context of the present invention (Arel et al., 2010, IEEE Computational Intelligence Magazine 5: pp. 13-18; Chen and Lin, 2014, IEEE Access 2: pp. 514-525). The basic concept of determining a stride feature by a machine learning algorithm is to define a regression function based on a first training data set for each stride feature to be determined and train the same with a data set (e.g. a data set of individual strides) for which the respective stride feature is known (e.g. determined by a method as described in the alternative above). This can then in a second step be applied to a second data set with unknown stride feature(s). In principle, any of the stride features herein including spatio-temporal/biomechanical and generic stride features may be determined. In one embodiment only spatio-temporal stride features may be determined by employing a machine learning algorithm. It is in particular also envisaged that the at least one stride feature derived by machine learning algorithms is/are selected from the group consisting of stride time, stride length, swing time, stance time, angle course, angle heel strike, angle toe off, clearance course, maximum toe clearance, minimum toe clearance, stride velocity, ground turning angle, medio-lateral sway, double support time and heel clearance course.

The advantage of employing a machine learning algorithm for stride feature determination is that it can be applied to any data segment representing a stride (in particular also the data segment directly resulting from the stride segmentation) without the requirement of determining stride events (where necessary).

A machine learning algorithm employed for determination of stride feature may, for example be generated and/or trained as follows:

In a supervised manner, a regression function linking raw sensor data (e.g. of a 3D-gyroscope and a 3D-accelerometer) of a stride (in principle any data segment representing a stride; e.g. as derived from stride segmentation) to one or more stride features is trained based on a training dataset. Such a training dataset may comprise or consists of a number of sensor data (e.g. of a 3D-gyroscope or a 3D-accelerometer) from individual strides annotated with respective stride features. Preferably, the training data set comprises at least 200, preferably at least 400, preferably at least 500, preferably at least 600, preferably at least 700, preferably at least 750, preferably at least 1000 and most preferably at least 1500 data segments representing single strides. A skilled person knows how to determine the minimal number of data segments that may be required in a certain training data set. This number may vary dependent on the specific stride feature which should be determined. Preferably, the training data set is derived or measured with a second sensor system that can directly measure the stride features of interest. If the data to be analyzed is derived from an eGaIT system, this external system may, for example, be an instrumented pressure matt as the GaitRite® (McDonough et al., 2001, Archives of Physical Medicine and Rehabilitation 82: pp. 419-25; Webster et al., 2005, Gait & Posture 22: pp. 317-321), a motion capture system (Windolf et al., 2008, Journal of Biomechanics 41: pp. 2776-2780) or any other measurement system that can annotate stride specific sensor data with the respective stride feature targeted in the regression.

The general principle of deep learning algorithms is, for example illustrated by Lapedes and Farber (Lapedes and Farber, 1988, Neural information processing systems pp. 442-456). The deep learning system that is trained with the annotated training data set in the context of determining at least one stride feature may, for example, be a convolutional neural network consisting of at least 2 convolutional layers followed by at least one fully connected layer and a readout layer. In practice, however, any network architecture that has at least 3 layers and enough nodes is able to learn every nonlinear function (Cybenko, 1989, Mathematics of control, signals and systems 2: pp. 303-314; Lapedes and Farber, 1988, Neural information processing systems pp. 442-456), e.g. the relationship between (any kind of) sensor data and one or more stride parameter(s).

In the training phase, standard stochastic learning optimizers such as, but not limited to stochastic gradient descent, may be used to track mismatches in the estimated target variable, i.e. a stride feature (e.g. stride length), back to changes in the model parameters, i.e. convolutional kernels or weights in the fully connected layers. Based on the random subset of training samples, the system observes in one iteration of the training loop how the neural network develops in order to minimize an error function. This error function could be the sum of root-mean-square errors between the estimated normalized/dimensionless stride parameters and the gold standard values from the external reference system. Normalization can, for example, be achieved by scaling the gold standard parameters the system learns to estimate to a range of [0,1] on the training set. Based on this transformation, estimated normalized/dimensionless stride features are later re-scaled to their physical dimensions.

Subsequently, a regression function between stride specific, normalized sensor data and the corresponding stride feature(s), e.g. stride length, can be found and can be applied to unseen data, i.e. data segments representing individual strides with unknown stride features. Optionally also a testing or evaluation may be performed with blinded data for which stride features are known but not fed into the system. Such testing and evaluation allows to estimate the precision of the trained regression algorithm and/or to determine if further training is required.

Alternatively, unsupervised methods can be used to extract a set of features from raw sensor data (e.g. of a 3D-gyroscope and a 3D-accelerometer) of a stride. These unsupervised methods comprise but are not limited to convolutional auto-encoders. Auto-encoders aim at finding a lower dimensional, latent representation of the input data that still allows reconstruction of the input signals. The latent representation thereby defines the data-driven feature set extracted from the incoming data segment or stride. Training of convolutional auto-encoders is performed analogue to supervised training by minimizing the reconstruction error between the input data and the reconstructed signal on a training dataset. The reconstruction error can, for example, be the sum of squared differences between the input data and the reconstruction.

When machine learning/deep learning algorithms are used, the input data segments have to be of fixed size (i.e. they have to be of a defined time segment). To achieve this, padding to a fixed size may be employed. Convolutional Networks have spatial/temporal invariance that is gained from the convolution operation. So they do not depend on the exact location of some information, i.e. the exact position of stride data in the padded input, but rather capture the information regardless of spatial/temporal location.

If data from different sensor systems (e.g. 3D-gyroscope and 3D-accelerometer) are used the input data is normalized with respect to the ranges of the gyroscope/accelerometer, such that the input signals are in the range [−1,1]. This ensures equal weighting between the different sensor types.

Otherwise, one sensor may outrule the other. For example, 3D-gyroscope information in range [−500,500]°/s would constantly outrule accelerometer information in the range [−6, 6] g. Normalization may be achieved by sample-wise division of input data with the respective sensor range.

In view of the above the present invention, in yet another embodiment provides for a method for determining one or more stride features, wherein said stride feature determination involves or is achieved by a machine learning/deep learning algorithm. Any of the mentioned embodiments applies mutatis mutandis.

Independent of how the step of determining one or more stride feature(s) for each stride or data segment representing at least one stride is performed (see alternatives above), said one or more stride features preferably are or preferably comprise stride time, stride length, swing time, stance time, angle course, angle heel strike, angle toe off, clearance course, maximum toe clearance, minimum toe clearance, stride velocity, ground turning angle, medio-lateral sway, double support time, heel clearance course, entropy, mean value, variance, root mean square, minimum, maximum, kurtosis, skewness, dominant frequency, energy in frequency band 0.5 to 3 Hz, energy in frequency band 3 to 8 Hz, energy ratio and/or signal energy. Even more preferably, said one or more stride features are or comprise stride length, angle heel strike, swing time, maximum toe clearance, stride velocity, root mean square, dominant frequency, energy in frequency band 3 to 8 Hz and/or entropy. Most preferably, said one or more stride features are or comprise stride length, maximum toe clearance and/or stride velocity, root mean square and/or entropy.

The methods of the present invention comprise in step d) defining one or more clusters (of strides or segments representing one or more strides) on the basis of at least one of the stride features determined in step c), wherein each cluster represents a class of strides. Similarly, the systems according to the present invention comprise a processor unit configured to perform step d) of the methods. Strides to be clustered may be strides (preferably each having an identifier like a number or being indexed by time at which the first HS in the data occurs) to which one or more of the first data segments are assigned. Data segments to be clustered may be the first data segments representing at least one (e.g. one or a sequence of consecutive strides). Clustering means that strides or data segments representing one or more strides are grouped in a way that those strides or data segments in the same group (called a cluster) are more similar (with respect to the stride features used for clustering and on the basis of the respective clustering techniques used and the metric involved) to each other than to those in other groups. In principle, clustering can be based on only one stride feature. Preferably, the clustering is, however, based on at least 2 stride features. In particular, it is also envisaged that the clustering in the context of the present invention takes into account at least 3 or all available stride features.

In general, for clustering strides into stride classes/types, the most important parameter that has to be determined from data is the number of clusters k. The general procedure, regardless of the specific clustering algorithm, is to loop over possible values of k and evaluate the clustering performance for each setting. Afterwards, the k that gives best clustering performance is selected as the number of clusters in the current dataset.

In the context of the present invention, clustering may comprise (or may be achieved) with a hierarchical clustering method, a centroid-based clustering method, a distribution- or density-based clustering method and/or artificial neural network techniques.

In the context of the present invention in principle any hierarchical clustering method may be used. Preferably, hierarchical clustering comprises or is performed with CURE and/or Agglomerative Clustering (Day and Edelsbrunner, 1984, Journal of Classification 1: pp. 7-24; Guha et al., 1998, SIGMOD Rec. 27: pp. 73-84).

In the context of the present invention in principle any centroid(-based) clustering algorithm known in the art can be employed (Jain et al., 1999, ACM computing surveys (CSUR) 31: pp. 264-323). Preferably, a centroid clustering technique employed for clustering in the context of the present invention is or comprises k-means, k-medians, k-means++ and/or fuzzy c-means (Jain et al., 1999, ACM computing surveys (CSUR) 31: pp. 264-323).

In the context of the present invention in principle any distribution- or density-based clustering algorithm known in the art can be employed. A distribution-based clustering analysis is based on distribution models. Clusters are defined as objects belonging most likely to the same distribution (e.g. a Gaussian or normal). In density-based clustering, clusters are defined as areas of higher density than the remainder of the data set. Objects in these sparse areas that are required to separate clusters are usually considered to be noise and border points. Preferably, a distribution or density based clustering technique employed for clustering in the context of the present invention is or comprises Mean-Shift, EM, DBSCAN, EnDBSCAN and/or OPTICS (Dempster et al., 1977, Journal of the royal statistical society. Series B (Methodological) pp. 1-38; Georgescu et al., 2003, Computer Vision, 2003. Proceedings. Ninth IEEE International Conference on pp. 456-463 vol. 1; Roy and Bhattacharyya, 2005, Distributed computing and internet technology pp. 523-535).

As illustrated also in the examples in one non-limiting embodiment clustering may be performed by using the k-means clustering algorithm (MacQueen, 1967, Proceedings of the fifth Berkeley symposium on mathematical statistics and probability 1: pp. 281-297). Evaluation of the clustering performance for different values of k, may be performed with the silhouette index (Rousseeuw, 1987, Journal of Computational and Applied Mathematics 20: pp. 53-65). In computing the silhouette index, the average dissimilarities of a given data-point to others from its cluster is compared to average dissimilarities of the same object to other clusters and tries to maximize this difference. The k with the best silhouette index determined the number of cluster, i.e. stride classes/types.

In one aspect, clustering in the context of the present invention may also comprise a principal component analysis (PCA) of said one or more stride features. In particular, such PCA may be performed before applying the clustering algorithms mentioned above in order to reduce the dimensionality before clustering. Principal component analysis (PCA) is a statistical procedure well known in the art. It uses an orthogonal transformation to convert a set of observations of possibly correlated variables into a set of values of linearly uncorrelated variables called principal components. The number of principal components is less than or equal to the number of original variables.

The clustering in the context of the present invention may also comprise application of a Dynamic Time Warping distance algorithm, which determines the Dynamic Time Warping distance to the average stride per cluster and/or the difference between the clusters. The advantage of this method is the identification of the straight walking cluster or other clusters where a template of the movement is available.

The methods of the present invention may further comprise a step of continuous monitoring of the clustering performance. Similarly, the system of the present invention may comprise a processor configured to perform such step.

In one aspect, continuous monitoring may, for example, comprise verification if enough strides or data segments representing one or more strides have been analyzed in order to define said one or more clusters with a certain predefined significance. For example, statistical group separation tests may be run continuously on the identified clusters to ensure unambiguous definition of a certain stride class/cluster at a predefined significance level. These group separation tests may in particular comprise or consist of analysis of variance known in the art. In particular, these group separation tests may also involve or consist of coefficient of error estimation. Examples for group separation tests comprise but are not limited to ANNOVA or t-test.

Similarly, in one aspect continuous monitoring may also comprise that the number of defined clusters is optimal based on a user input.

An alternative approach to monitor the continuous clustering performance is the computation of inter- and intra-cluster variations and to compare the two. In one aspect, if a distribution or density based clustering method is employed for clustering also a log-likelihood or perplexity may be used for monitoring clustering performance.

In general the continuous monitoring/verification of the clustering performance may involve determination of an inter- and intra-class distances, Dunn index, Davies-Bouldin index, Silhouette value and/or statistical group separation tests such as but not limited to ANNOVA or t-test.

The clusters/classes of strides defined during clustering in the context of the present invention may define distinct stride types. In particular, one cluster of the one or more defined clusters may represent a class of typical strides of the subject. Typical in this context means that this class represents the cluster/class with the most strides or data segments. In other words, this is a cluster/class representing the most frequent strides. If the 3D-movement data comprises long movement sequences, e.g. continuous monitoring over several hours, days or years, the typical class of strides may in particular represent the characteristic stride of a subject.

Other none limiting examples for stride types that may be represented by the clusters/classes defined by clustering may be strides of straight walking, strides of walking initiation, strides of a turning movement or strides of walking stairways. As mentioned above this list is non-limiting. In principle, any type of strides present in the 3D-movement sequence comprised in the data to be analyzed by the method or system of the present invention may be represented by a cluster/class.

The clusters defined by clustering can in principle comprise any number of strides. The number of strides basically depends on the number of strides comprised in the 3D-movement data employed for the analysis, i.e. the number of strides per cluster is merely data-driven. However, it is particularly also envisaged that each of the one or more clusters comprises at least 5 strides (or data segments representing one or more strides).

The methods of the present invention may further comprise a step of determining averaged stride features for at least one or all of said one or more stride clusters by averaging the stride features over each of the respective cluster(s). In other words an average value for one or more stride feature may be calculated by averaging the values for the respective stride feature(s) of all strides belonging to a cluster. In this context in particular also a variance may be determined. The variance can indicate the homogeneity or heterogeneity, respectively, between strides of a cluster for the averaged stride feature. The determination of average stride features may be performed for all determined stride features or a subset thereof. However, also only stride features that have not been used for clustering but have been determined can be averaged.

In one aspect, the systems and methods of the present invention may also comprise means or steps for comparing two of the defined clusters of strides (or clusters of the (first) data segments representing one or more strides) and thereby identifying at least one stride feature of said one or more stride features that differs more than 20%, more than 30%, more than 40%, or more than 50% between the two clusters. Such stride feature may subsequently be defined as a stride feature which is different between the two stride types. This embodiment may be of particular importance when the gait analysis methods or systems of the present invention are used for assessing gait impairments of a subject. In particular identifying one or more stride features that are particularly different between the clusters (see cut-offs above) may draw the physician's attention to particular details (stride features) when manually assessing gait of a subject. In particular, certain gait impairments may be localized by identifying different stride features by comparing a cluster representing "healthy" strides of a subject with "impaired" strides of a subject.

It is particularly also envisaged that the method of the present invention may comprise, after clustering, generating an artificial sequence of concatenating strides from strides belonging to the same cluster/class.

Accordingly, in one aspect the method of the present invention may comprise after clustering identifying second data segments for several or each of the first data segments of a defined cluster, wherein each of said second data segments represents an integer number of strides (e.g. 1, 2, 3, 4, 5 or more strides), preferably one stride. For example, the second data segments may represent two strides. Most preferably, however, each of the second data segments represents one stride. If the first data segment comprises more than one (e.g. two) strides and the second data segment comprises one stride, the one stride of the second data segment is preferably the first of said more than one (e.g. two strides of the first data segment. In this context in principle any definition of one stride may be employed. In particular, in one embodiment the definition as received directly by stride segmentation may be used. In another embodiment one stride may be defined by two consecutive heel strike to heel strike events.

The methods of the present invention may further comprise concatenating the second data segments in order to generate an artificial 3D-movement sequence comprising several (e.g. at least 3, at least 4 at least 5 at least 6 or at least 10) consecutive strides. In other words strides of one cluster may be artificially assembled to a consecutive gait sequence. This can, for example, be achieved by directly assembling the second data segments which represent an integer number of strides with each other. In one embodiment the artificial gait sequence may also be monitored on a screen. Assembling artificial gait sequences has the advantage that gait sequences which only comprise strides with similar features are generated. This may for example allow a physician to more easily recognize certain gait impairments of a subject. This is particularly the case if the gait impairment is of rather low frequency and only occurs rarely between normal strides. Similarly, an (artificially) generated sequence of strides (gait sequence) allows determining stride sequence features (which is not possible with individual strides).

An artificial sequence of concatenating strides may alternatively also be defined by defining/calculating a data segment representing an average stride/stride sequence of a cluster of strides/stride sequences and subsequently concatenating at least two, preferably at least 5 or most preferably at least 10 of the defined/calculated average data segment to generate an artificial stride sequence/3D-movement sequence of a foot. Defining/calculating a data segment representing an average stride/stride sequence may be achieved by averaging the underlying raw data of corresponding data segments of a cluster. For instance if a three-axis gyroscope signal and a three-axis accelerometer signal are employed, one or more, preferably all of the axes may be averaged.

The methods of the present invention may further comprise determining from an (artificially) generated 3D-movement sequence one or more stride features. The stride features may be or may comprise stride time, stride length, swing time, stance time, angle heel strike, angle toe off, maximum toe clearance, stride velocity, entropy, mean value, variance, root mean square, minimum, maximum, kurtosis, skewness, dominant frequency, energy in frequency band 0.5 to 3 Hz, energy in frequency band 3 to 8 Hz, energy ratio and/or signal energy. The determination of stride features is achieved as described above with the only exception that the (artificially) generated 3D-movement sequence is used as data.

The methods of the present invention may also comprise determining a score which combines at least two generic or biomechanical stride features of the strides/data segments of one cluster or artificial gait sequence defined based on one cluster. Such score may in particular be a score that represents an indication if a person suffers from a certain motion impairing disease and/or movement impairment. To build such a score, stride features together with a clinical rating of a certain movement impairment may be used to train a regression algorithm like support vector regression, linear regression, locally weighted linear regression, robust regression, additive regression, logistic regression (Witten and Frank, 2005, pp.).

The method for analyzing gait of a subject may in principle be performed for only one foot. However, it is also particularly envisaged that the 3D-movement of both feet of a subject are analyzed. By alignment of the sensor axes (as described elsewhere herein) even a comparison of strides of the two feet are possible.

As mentioned herein, first data segments representing one or more strides may be defined in method of the present invention and stride features may be defined for said first data segments. The one or more stride features of one or more partially overlapping first data segments may be assigned to the same stride, and in step d) of the method these strides are clustered. The overlapping first data segments may in particular be heel-strike to heel-strike events, mid-stance to mid-stance events and/or toe-off to toe-off events of two consecutive strides.

Accordingly, in accordance with a further aspect a method for analyzing gait of a subject according to the present invention may comprise:
a) providing data representing the 3D-movement of a foot of said subject over time, wherein said 3D-movement comprises a plurality of strides of said foot;
b) identifying within said data first data segments, wherein each of said first data segments represents at least one stride;
c) determining one or more stride features for strides represented by or by a section of said first data segments; and
d) defining one or more clusters of strides on the basis of at least one stride feature of the one or more stride features as determined in c), wherein each cluster represents a class of strides.

In accordance with another aspect the method of the present invention may also comprise:
a) providing data representing the 3D-movement of a foot of said subject over time, wherein said 3D-movement comprises a plurality of strides of said foot;
b) identifying within said data first data segments, wherein each of said first data segments represents one stride, identifying within said data second data segments, wherein each of said second data segments represents one stride, and wherein one stride is represented by one of said first data segments and one of said second data segments;
c) determining one or more stride features for each of the strides represented by said one or more first and/or second data segments; and
d) defining one or more clusters of strides on the basis of at least one stride feature of said one or more stride features, wherein each cluster represents a class of strides.

In other words, a single stride may be represented by two or more different data segments due to two or more different definitions of the stride (e.g., heel strike to heel strike, toe off to toe off, mid stance to mid stance, or the definition as derived from stride segmentation as described above (e.g. a data segment as shown in FIG. 7)). Of course, more than two definitions may be used to define further data segments. The first and/or second data segments may also represent a section or part of a stride cycle.

Any of the preferred features discussed above with respect to various embodiments of the method can be combined with these two further aspects of the invention.

As already mentioned above, the present invention also relates to a system configured to perform the methods of the present invention. This system may comprise any means to perform any embodiment of the methods mentioned herein. The embodiments described herein for the method of the present invention apply mutatis mutandis to the system.

In particular, the system for analyzing gait of a subject of the present invention may comprise:
a) an input for data representing the 3D-movement of a foot of said subject, wherein said 3D-movement comprises a plurality of strides of said foot;
b) one or more processing units capable of:
    identifying within said data first data segments, wherein each of said first data segments represents at least one stride;
    determining one or more stride features for each of said first data segments; and
    defining one or more clusters on the basis of at least one of the one or more determined stride feature(s), wherein each cluster represents a class of strides.

These process steps may be performed within one and the same processing unit or in different processing units. Preferably, the one or more processing units are capable of performing any one or any combination of the method steps claimed by the method claims or described above with respect to preferred embodiments of the method of the invention.

The system (or a kit comprising the system) may further comprise a measuring unit, which is adapted to be mounted to a foot of a subject, preferably to a shoe, more preferably to a lateral side of a shoe, said measuring unit being adapted for providing data representing the 3D-movement of a foot of said subject, wherein said 3D-movement comprises a plurality of strides of said foot. Said measurement unit may, e.g., comprise a clip or other fixation device for reversibly mounting the measurement unit to a shoe. Said measurement unit may further comprise a 3D-accelerometer and/or a 3D-gyroscope. Said measurement unit may further comprise a transmitter unit adapted to transmit the data to a respective receiver connected to the one or more processing units.

The present invention in particular also relates to the following aspects:

1. A method for analyzing gait of a subject, said method comprising:
   a) providing data representing the 3D-movement of a foot of said subject over time, wherein said 3D-movement comprises a plurality of strides of said foot;
   b) identifying within said data first data segments, wherein each of said first data segments represents at least one stride;
   c) determining one or more stride features for each of said first data segments; and
   d) defining one or more clusters on the basis of at least one stride feature of said one or more stride features, wherein each cluster represents a class of strides.
2. The method of aspect 1, wherein said subject suffers from impaired motion, preferably impaired gait.
3. The method of aspect 1 or 2, wherein said subject suffers from a disease that impairs motion, preferably a neurological disease, a musculo-skeletal disease and/or a cardio-pulmonal disease and/or wherein said subject suffers from complex causes of movement impairment preferably resulting from geriatric diseases, mono- to polytrauma, monoarticulate orthopedic diseases or systemic orthopedic diseases.
4. The method of any one of the preceding aspects, wherein said subject suffers from a neurological disease selected from the group consisting of Parkinson's disease, Multiple Sclerosis, Huntington's disease, Spastic Paraplegia, Ataxia, Stroke, Dystonia, Chorea, Drug-induced movement disorders, Cerebral Palsy, Pain syndroms and Polyneuropathies; and/or a complex movement impairment resulting from a geriatric disease selected from the group consisting of Sarcopenia and Fraility; and/or a musculo-skeletal disease selected from the group consisting of muscle, bone and/or joint Traumata, Myopathy, Myositis, Osteopathie, Osteoporosis, Osteoarthrosis, Rheumatological diseases and Osteoathritis.
5. The method of any one of the preceding aspects, wherein said data comprises or consists of signals that are obtainable from a 3D-accelerometer and/or a 3D-gyroscope.
6. The method of any one of the preceding aspects, wherein said data is retrieved from the internet and/or an intranet.
7. The method of any one of the preceding aspects, wherein a) comprises measuring said data.
8. The method of aspect 7, wherein said measuring involves using a 3D-accelerometer and/or a 3D-gyroscope.
9. The method of aspect 7 or 8, wherein said 3D-accelerometer and/or 3D-gyroscope is/are disposed on a lateral side of a shoe worn by said subject so that the 3D-accelerometer and/or 3D-gyroscope are disposed below the ankle joint of said subject.
10. The method of any one of the preceding aspects, wherein b) comprises comparing said data with a predefined data set.
11. The method of aspect 10, wherein said predefined data set is adapted to a type of impaired motion.
12. The method of aspect 10 or 11, wherein said predefined data set is adapted to said subject.
13. The method of anyone of aspects 10 to 12, wherein b) involves using an algorithm comprising a Hidden Markov Model, a Robust event detection, a Subsequence Dynamic Time Warping, a Conditional Random Field Algorithm, a Longest Common Subsequence Algorithm, a Deep learning algorithm and/or a Threshold or Matched Filter/Cross-correlation.
14. The method of any one of the preceding aspects, wherein each of said first data segments represents at most three, preferably at most two strides.
15. The method of any one of the preceding aspects, wherein each of said first data segments represents at least 1.5 strides.
16. The method of any one of the preceding aspects, wherein each of said first data segments represents two strides.
17. The method of any one of the preceding aspects, wherein said stride is defined as a mid-stance to mid-stance event or a heel-strike to heel-strike event.
18. The method of any one of the preceding aspects, wherein at least two or preferably at least three stride features are determined in c) and used in d).
19. The method of any one of the preceding aspects, wherein said one or more stride features are or comprise biomechanical stride features and/or generic features.
20. The method of aspect 19, wherein said biomechanical stride features are selected from the group consisting of stride time, stride length, swing time, stance time, angle course, angle heel strike, angle toe off, clearance course, maximum toe clearance, minimum toe clearance stride velocity, ground turning angle, medio-lateral sway, double support time and heel clearance course.
21. The method of aspect 19 or 20, wherein said generic features are selected from the group consisting of entropy, mean value, variance, root mean square, minimum, maximum, kurtosis, skewness, dominant frequency, energy in frequency band 0.5 to 3 Hz, energy in frequency band 3 to 8 Hz, energy ratio, signal energy.
22. The method according to any of the preceding aspects, wherein in c) determining at least one of said one or more stride features involves a machine learning algorithm, preferably a machine learning algorithm selected from the group consisting of Deep Neural Network, Deep Convolutional Neural Networks, Deep Belief Network, Convolutional Deep Belief Network and/or Multilayer-Kernel-Machines.
23. The method of aspect 22, wherein said at least one stride feature derived by machine learning algorithms is/are selected from the group consisting of stride time, stride length, swing time, stance time, angle course, angle heel strike, angle toe off, clearance course, maximum toe clearance, minimum toe clearance, stride velocity, ground turning angle, medio-lateral sway, double support time and heel clearance course.
24. The method of any one of the preceding aspects, wherein said one or more stride features are or comprise stride time, stride length, swing time, stance time, angle course, angle heel strike, angle toe off, clearance course, maximum toe clearance, minimum toe clearance, stride velocity, ground turning angle, medio-lateral sway, double support time, heel clearance course, entropy, mean value, variance, root mean square, minimum, maximum, kurtosis, skewness, dominant frequency, energy in frequency band 0.5 to 3 Hz, energy in frequency band 3 to 8 Hz, energy ratio and/or signal energy.

25. The method of any one of the preceding aspects, wherein said one or more stride features are or comprise stride length, angle heel strike, swing time, maximum toe clearance, stride velocity, root mean square, dominant frequency, energy in frequency band 3 to 8 Hz and/or entropy.

26. The method of any one of the preceding aspects, wherein said one or more stride features are or comprise stride length, maximum toe clearance, stride velocity, root mean square and/or entropy.

27. The method of any one of the preceding aspects, wherein d) comprises a principal component analysis (PCA) of said one or more stride features.

28. The method of any one of the preceding aspects, wherein in d) at least two clusters are defined and wherein d) comprises determination of a Dynamic Time Warping distance between the clusters.

29. The method of any one of the preceding aspects, wherein d) comprises using an Artificial Neural Network technique (e.g. Self Organizing Maps).

30. The method of any one of the preceding aspects, wherein d) comprises using a hierarchical clustering technique, a centroid-based clustering technique and/or a distribution or density based clustering technique.

31. The method of aspect 30, wherein said hierarchical clustering technique is or comprises CURE and/or Agglomerative Clustering.

32. The method of aspect 30, wherein said centroid-based clustering technique is or comprises k-means, k-medians, k-means++ and/or fuzzy c-means.

33. The method of aspect 30, wherein said distribution-based or density-based clustering technique is or comprises Mean-Shift, EM, DBSCAN, EnDBSCAN and/or OPTICS.

34. The method of any one of the preceding aspects, wherein said method further comprises verifying if enough of said first data segments have been analyzed for defining said one or more clusters with a certain predefined significance.

35. The method of any one of the preceding aspects, wherein said method further comprises verifying if the number of defined clusters is optimal based on a user input.

36. The method of aspect 34 or 35, wherein said verifying involves determining an inter-class distance and/or intra-class distance and/or Dunn index and/or Davies-Bouldin index and/or Silhouette value.

37. The method of any one of the preceding aspects, wherein one cluster of said one or more clusters represents a class of typical strides of the subject.

38. The method of aspect 37, wherein said one cluster is defined as the cluster with the most strides.

39. The method of any one of the preceding aspects, wherein one cluster of said one or more clusters represents a class of at least 5 strides of the subject.

40. The method of any one of the preceding aspects, one cluster of said one or more clusters represents a class of strides representative for straight walking strides, walking initiation strides, turning movement strides or stairways walking strides.

41. The method of any one of the preceding aspects, wherein said method further comprises generating averaged stride features for at least one or all of said one or more stride clusters by averaging the stride features over each of the respective cluster(s).

42. The method of any one of the preceding aspects, wherein at least 2, preferably 3 of said clusters of said first data segments are defined.

43. The method of aspect 42, wherein said method further comprises comparing two clusters of said first data segments and identifying at least one stride feature of said one or more stride features that differs more than 20%, more than 30%, more than 40%, or more than 50% between the two clusters.

44. The method of any one of the preceding aspects, wherein said method further comprises identifying second data segments for several or each of said first data segments within one cluster, wherein each of said second data segments represents an integer number of strides, preferably one stride.

45. The method of aspect 44, wherein each of the first data segments represents more than one (e.g. two) strides and each of the second data segments represents one stride.

46. The method of aspect 44 or 45, wherein said one stride is defined as a heel strike to heel strike event.

47. The method of any one of aspects 44 to 46, wherein said method further comprises concatenating the second data segments in order to generate a 3D-movement sequence comprising several consecutive strides.

48. The method of aspect 47, wherein said method further comprises determining one or more stride sequence features from the generated 3D-movement sequence.

49. The method of aspect 48, wherein said one or more stride sequence features are or comprise stride time, stride length, swing time, stance time, angle heel strike, angle toe off, maximum toe clearance, cadence, stride velocity, entropy, mean value, variance, root mean square, minimum, maximum, kurtosis, skewness, dominant frequency, energy in frequency band 0.5 to 3 Hz, energy in frequency band 3 to 8 Hz, energy ratio and/or signal energy.

50. The method of aspect 48, wherein said one or more stride sequence features are or comprise stride time, stride length, swing time, stance time, angle heel strike, angle toe off, maximum toe clearance, entropy, variance, root mean square, maximum, skewness, dominant frequency, energy in frequency band 3 to 8 Hz, energy ratio and/or signal energy.

51. The method of aspect 48, wherein said one or more stride sequence features are or comprise at least angle toe off, maximum and/or dominant frequency.

52. The method of any one of aspects 48 to 51, wherein at least two stride sequence features are determined.

53. The method of aspect 52, wherein said method further comprises determining a score which combines at least two stride sequence features.

54. The method of any one of the preceding aspects, wherein said method is performed for both feet of a subject.

55. The method of any one of the preceding aspects, wherein said one or more stride features of one or more partially overlapping first data segments are assigned to the same stride, and wherein in d) these strides are clustered.

56. The method of aspect 55, wherein said one or more partially overlapping first data segments are heel-strike to heel-strike events, mid-stance to mid-stance events and/or toe-off to toe-off events of two consecutive strides.

57. A system for analyzing gait of a subject, said system comprising:
   a) an input for data representing the 3D-movement of a foot of said subject, wherein said 3D-movement comprises a plurality of strides of said foot;
   b) one or more processing units being configured for:
      identifying within said data first data segments, wherein each of said first data segments represents at least one stride;
      determining one or more stride features for each of said first data segments; and
      defining one or more clusters on the basis of at least one of the one or more determined stride feature(s), wherein each cluster represents a class of strides.
58. The system of aspect 57, wherein said system further comprises a measurement system comprising one or more sensors adapted for recording said data representing the 3D-movement of a foot of said subject.
59. The system of aspect 58, wherein said measurement system is a mobile measurement system.
60. The system of any of aspects 57 to 59 wherein said input is configured to retrieve data from the internet and/or an intranet.
61. The system of aspect 59, wherein the mobile measurement system and the input are configured for transferring the data representing the 3D-movement of a foot of said subject from the mobile measurement system to the input via a wireless connection, preferably bluetooth.
62. The system of any of the aspects 58 to 61, wherein said measurement system comprises a 3D-accelerometer and/or a 3D-gyroscope.
63. The system of any of the aspects 58 to 62, wherein said measurement system is adapted to be mounted to a foot of a subject, preferably to a shoe, more preferably to a lateral side of a shoe or wherein said system further comprises a shoe on which said measurement system is disposed, preferably on a lateral side at a position which is located below the ankle joint of a subject in the worn state.
64. The system of aspects 57 to 63, wherein said processing unit is configured to compare said data with a predefined data set in order to identify within said data said first data segments.
65. The system of aspect 64, wherein said system further comprises a memory containing the predefined data set, wherein said predefined data set is adapted to a type of impaired motion.
66. The system of aspect 64 or 65, wherein said system further comprises a memory containing the predefined data set, wherein said predefined data set is adapted to said subject.
67. The system of anyone of aspects 64 to 66, wherein said processing unit is configured to identify within said data said first data segments by using an algorithm comprising a Hidden Markov Model, a Robust event detection, a Subsequence Dynamic Time Warping, a Conditional Random Field Algorithm, a Longest Common Subsequence Algorithm, a Deep learning algorithm and/or a Threshold or Matched Filter/Cross-correlation.
68. The system of any one of aspects 57 to 67, wherein each of said first data segments represents at most three, preferably at most two strides.
69. The system of any one of aspects 57 to 68, wherein each of said first data segments represents at least 1.5 strides.
70. The system of any one of aspects 57 to 69, wherein each of said first data segments represents two strides.
71. The system of any one of aspects 57 to 70, wherein said stride is defined as a mid-stance to mid-stance event or a heel-strike to heel-strike event.
72. The system of any one of aspects 57 to 71, wherein the processor unit is configured for determining at least two or preferably at least three stride features and for defining said one or more clusters based on at least two or preferably at least three stride features.
73. The system of any one of aspects 57 to 72, wherein said one or more stride features are or comprise biomechanical stride features and/or generic features.
74. The system of aspect 73, wherein said biomechanical stride features are selected from the group consisting of stride time, stride length, swing time, stance time, angle course, angle heel strike, angle toe off, clearance course, maximum toe clearance, minimum toe clearance, stride velocity, ground turning angle, medio-lateral sway, double support time and heel clearance course.
75. The system of aspect 73, wherein said generic features are selected from the group consisting of entropy, mean value, variance, root mean square, minimum, maximum, kurtosis, skewness, dominant frequency, energy in frequency band 0.5 to 3 Hz, energy in frequency band 3 to 8 Hz, energy ratio, signal energy.
76. The system of any of aspects 57 to 75, wherein said processing unit is configured to determine at least one of said one or more stride features by a machine learning algorithm, preferably a machine learning algorithm selected from the group consisting of Deep Neural Network, Deep Convolutional Neural Networks, Deep Belief Network, Convolutional Deep Belief Network and/or Multilayer-Kernel-Machines.
77. The system of aspect 76, wherein said at least one stride feature derived by machine learning algorithms is/are selected from the group consisting of stride time, stride length, swing time, stance time, angle course, angle heel strike, angle toe off, clearance course, maximum toe clearance, minimum toe clearance, stride velocity, ground turning angle, medio-lateral sway, double support time and heel clearance course.
78. The system of any of aspects 57 to 76, wherein said one or more stride features are or comprise stride time, stride length, swing time, stance time, angle course, angle heel strike, angle toe off, clearance course, maximum toe clearance, minimum toe clearance, stride velocity, ground turning angle, medio-lateral sway, double support time, heel clearance course, entropy, mean value, variance, root mean square, minimum, maximum, kurtosis, skewness, dominant frequency, energy in frequency band 0.5 to 3 Hz, energy in frequency band 3 to 8 Hz, energy ratio and/or signal energy.
79. The system of any one of aspects 57 to 76, wherein said one or more stride features are or comprise stride length, angle heel strike, swing time, maximum toe clearance, stride velocity, root mean square, dominant frequency, energy in frequency band 3 to 8 Hz and/or entropy.
80. The system of any of aspects 57 to 76, wherein said one or more stride features are or comprise stride length, maximum toe clearance and/or stride velocity, root mean square and/or entropy.
81. The system of any of aspects 57 to 80, wherein said processing unit is configured to define one or more clusters using a principal component analysis (PCA) of said one or more stride features.

82. The system of any of aspects 57 to 81, wherein said processing unit is configured to define at least two clusters by determination of a Dynamic Time Warping distance between the two clusters.
83. The system of any of aspects 57 to 82, wherein said processing unit is configured to define one or more clusters using an Artificial Neural Network technique.
84. The system of any of aspects 57 to 83, wherein said processing unit is configured to define one or more clusters using a hierarchical clustering technique, a centroid-based clustering technique and/or a distribution or density based clustering technique.
85. The system of aspect 84, wherein said hierarchical clustering technique is or comprises CURE and/or Agglomerative Clustering.
86. The system of aspect 84, wherein said centroid-based clustering technique is or comprises k-means, k-medians, k-means++ and/or fuzzy c-means.
87. The system of aspect 84, wherein said distribution-based or density-based clustering technique is or comprises Mean-Shift, EM, DBSCAN, EnDBSCAN and/or OPTICS.
88. The system of any of aspects 57 to 87, wherein said one or more processor units are further configured for verifying if enough of said first data segments have been analyzed for defining said one or more clusters with a certain predefined significance.
89. The system of any of aspects 57 to 88, wherein said one or more processor units are further configured for verifying if the number of defined clusters is optimal.
90. The system of aspect 88 or 89, wherein said verifying involves determining an inter-class distance and/or intra-class distance and/or Dunn index and/or Davies-Bouldin index and/or Silhouette value.
91. The system of any of aspects 57 to 90, wherein one cluster of said one or more clusters represents a class of typical (i.e. the most frequent) strides of the subject.
92. The system of aspect 91, wherein said one cluster is defined as the cluster with the most strides.
93. The system of any of aspects 57 to 92, wherein one cluster of said one or more clusters represents a class of at least 5 strides of the subject.
94. The system of aspect 91, wherein said one cluster is defined as the cluster with strides representative for straight walking, walking initiation, turning movement or walking stairways.
95. The system of any of aspects 57 to 94, wherein said one or more processor units are further configured for generating averaged stride features for at least one or all of said one or more stride clusters by averaging the stride features over each of the respective cluster(s).
96. The system of any of aspects 57 to 95, wherein said defining of one or more clusters comprises defining at least 2, preferably 3 of said clusters of said first data segments are defined.
97. The system of aspect 96, wherein said one or more processor units are further configured for comparing two clusters of said first data segments and identifying at least one stride feature of said one or more stride features that differs more than 20%, more than 30%, more than 40%, or more than 50% between the two clusters.
98. The system of any of aspects 57 to 97, wherein said one or more processor units are further configured for identifying second data segments for several or each of said first data segments within one cluster, wherein each of said second data segments represents an integer number of strides, preferably one stride.
99. The system of aspect 98, wherein each of the first data segments represents two strides and each of the second data segments represents one stride.
100. The system of aspect 98 or 99, wherein said one stride is defined as a heel strike to heel strike event.
101. The system of any of aspects 98 to 100, wherein said one or more processor units are further configured for concatenating the second data segments in order to generate a 3D-movement sequence comprising several consecutive strides.
102. The system of aspect 101, wherein said one or more processor units are further configured for determining one or more stride sequence features from the generated 3D-movement sequence.
103. The system of aspect 102, wherein said one or more stride sequence features are or comprise stride time, stride length, swing time, stance time, angle heel strike, angle toe off, maximum toe clearance, cadence, stride velocity, entropy, mean value, variance, root mean square, minimum, maximum, kurtosis, skewness, dominant frequency, energy in frequency band 0.5 to 3 Hz, energy in frequency band 3 to 8 Hz, energy ratio and/or signal energy.
104. The system of aspect 102, wherein said one or more stride sequence features are or comprise stride time, stride length, swing time, stance time, angle heel strike, angle toe off, maximum toe clearance, entropy, variance, root mean square, maximum, skewness, dominant frequency, energy in frequency band 3 to 8 Hz, energy ratio and/or signal energy.
105. The system of aspect 102, wherein said one or more stride sequence features are or comprise at least angle toe off, maximum and/or dominant frequency.
106. The system of any of aspects 102 to 105, wherein at least two stride sequence features are determined.
107. The system of aspect 106, wherein said method further comprises determining a score which combines at least two stride sequence features.
108. The system of any of aspects 57 to 107, wherein said system is adapted for analyzing the 3D-movement of both feet of said subject.
109. Use of a system as defined in any of aspects 57 to 108, for gait analysis of a subject that suffers from impaired motion, preferably impaired gait.
110. The use of aspect 109, wherein said subject suffers from a disease that impairs motion, preferably a neurological disease, a musculo-skeletal disease and/or a cardio-pulmonal disease and/or wherein said subject suffers from complex causes of movement impairment preferably resulting from geriatric diseases, mono- to polytrauma, monoarticulate orthopedic diseases or systemic orthopedic diseases.
111. The use of aspect 110, wherein said subject suffers from a neurological disease selected from the group consisting of Parkinson's disease, Multiple Sclerosis, Huntington's disease, Spastic Paraplegia, Ataxia, Stroke, Dystonia, Chorea, Drug-induced movement disorders, Cerebral Palsy, Pain syndroms and Polyneuropathies; and/or a complex movement impairment resulting from a geriatric disease selected from the group consisting of Sarcopenia and Fraility; and/or a musculo-skeletal disease selected from the group consisting of muscle, bone and/or joint Traumata, Myopathy, Myositis, Osteopathie, Osteoporosis, Osteoarthrosis, Rheumatological diseases and Osteoathritis.

112. Computer program product containing information for performing any of the methods according to aspects 1 to 56.

113. The method of any one of aspects 1 to 56, wherein b) comprises:
(i) identifying strides in said data of a); and
(ii) defining the first data segments, wherein each of the first data segments comprises one stride or a sequence of consecutive strides of the strides identified in (i), preferably at most two consecutive strides of the strides identified in (i).

114. The method of any one of aspects 1 to 56 or 113, wherein each of said first data segments comprises at least two consecutive heel-strike events and/or at least two consecutive mid-stance events.

115. The method of any one of aspects 1 to 56, 113 or 114, wherein each of said first data segments comprises at most two consecutive heel-strike events and/or at most two consecutive mid-stance events.

116. The system of any one of aspects 57 to 108, wherein being configured for identifying within said data first data segments comprises being configured for:
(i) identifying strides in said data of a); and
(ii) defining the first data segments, wherein each of the first data segments comprises one stride or a sequence of consecutive strides of the strides identified in (i), preferably at most two consecutive strides of the strides identified in (i).

114. The system of any one of aspects 57 to 108 or 116, wherein said one or more processing units is configured to identify said first data segments so that each of said first data segments comprises at least two consecutive heel-strike events and/or at least two consecutive mid-stance events.

115. The method of any one of aspects 57 to 108, 116 or 117, wherein said one or more processing units is configured to identify said first data segments so that each of said first data segments comprises at most two consecutive heel-strike events and/or at most two consecutive mid-stance events.

The present invention is further described by reference to the following non-limiting figures and examples.

The Figures show:

FIG. 1: Shown is a Shimmer® 3 sensor unit mounted with custom designed clip on the lateral side of a regular sport shoe as used in Example 1. The Shimmer 3 sensor unit was developed by Shimmer sensing (Dublin, Ireland) and includes a tri-axial (3D) gyroscope (InvenSense MPU9150, range of ±1000°/s, sensitivity of 16LSB/°s) and a tri-axial (3D) accelerometer (STMicroelectronics LSM303DLHC, range of ±8 g, sensitivity of 83 LSB/g) The directions of the sensor axes are shown accordingly to the sensor placement on the shoe (a): accelerometer; b): gyroscope).

Figure 2:
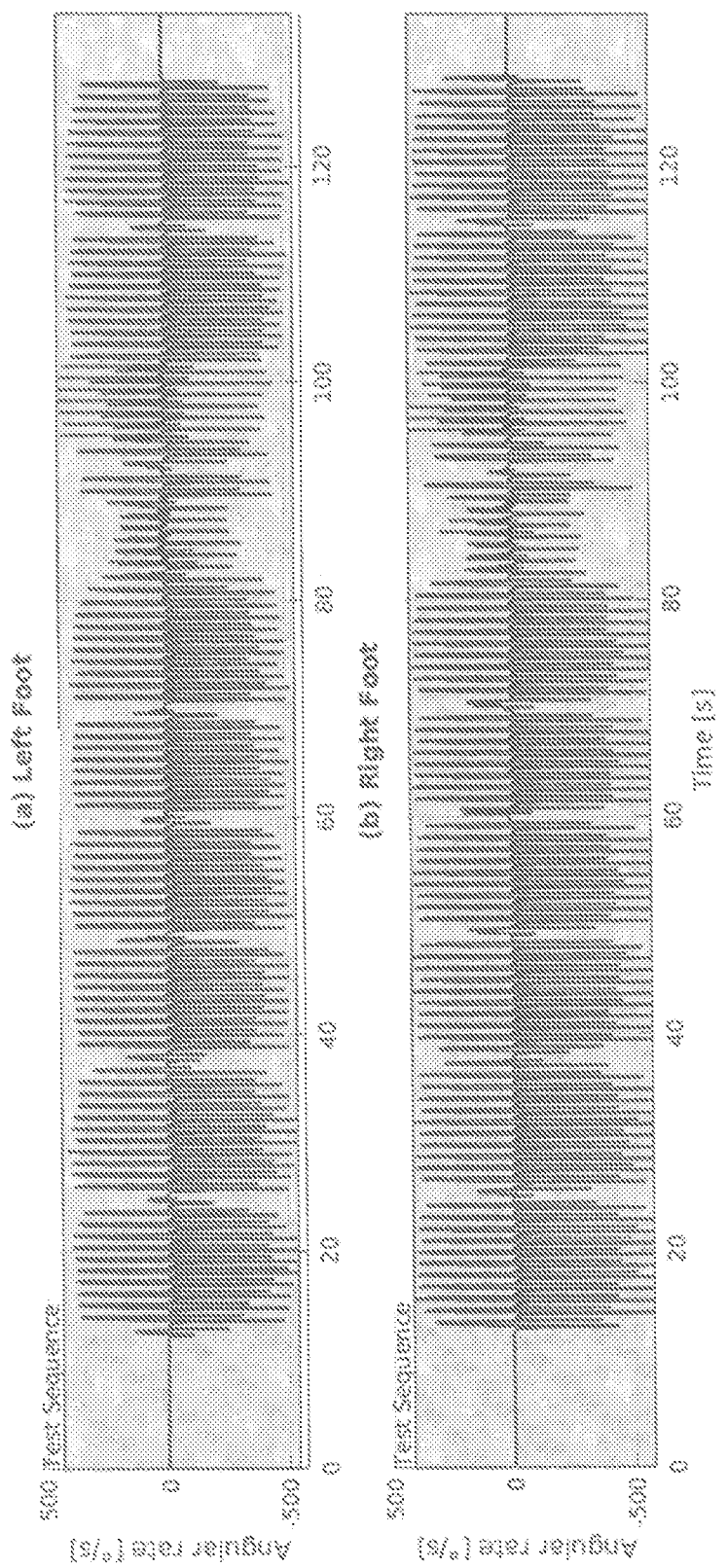

FIG. 2: Shown is angular rate in sagittal plane, also referred herein as GZ axis, (gyroscope data) recorded from a young man over 130 seconds. Data of the left and the right foot is shown. Data has been preprocessed by axis alignment and sensor calibration as described in the appended example.

Figure 3:
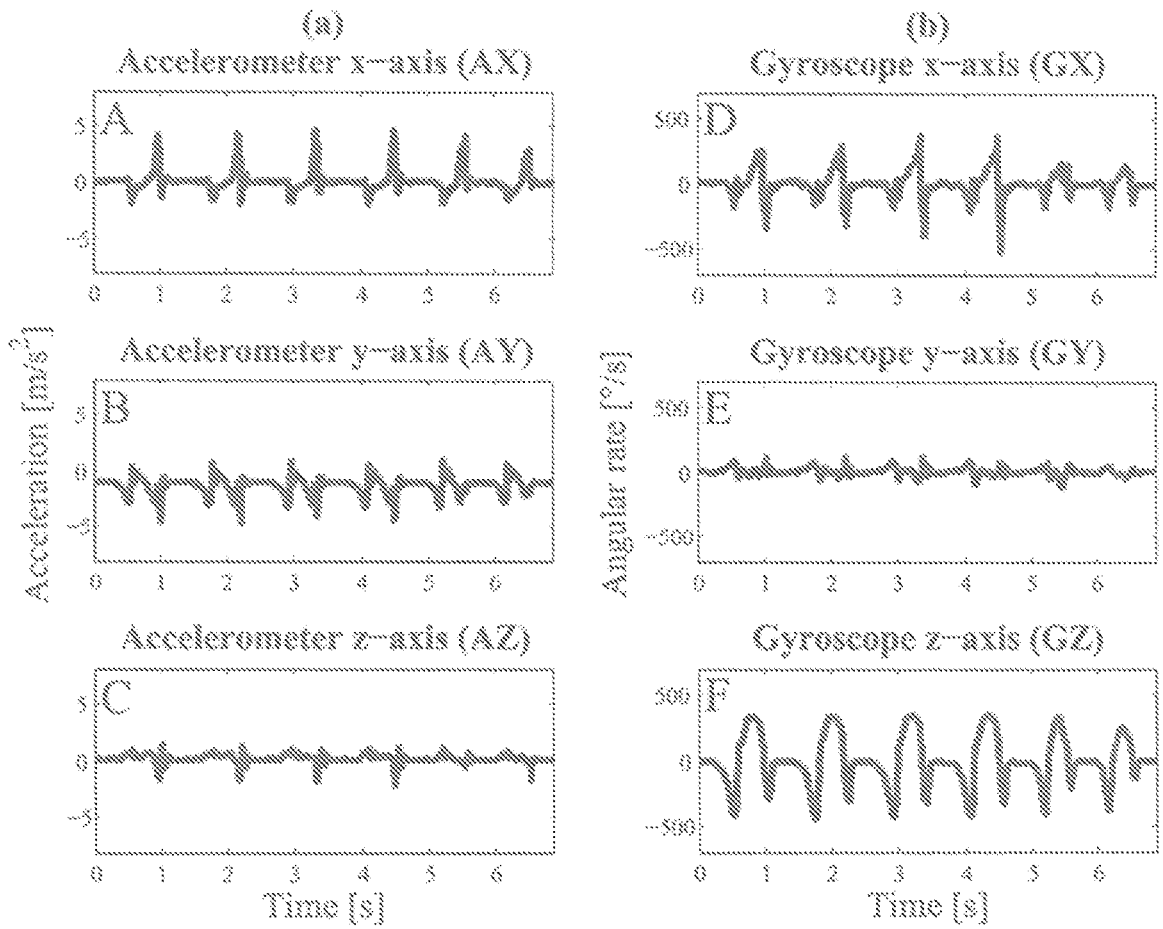

FIG. 3: Typical sensor signals of five strides (enhanced sequence of the signal from left foot in FIG. 2). Column (a) shows accelerometer signals from movements in A) anterior-posterior, B) inferior-superior and C) lateral-medial direction. Column (b) shows gyroscope angular velocities of the rotations in D) coronal, E) transverse and F) sagittal plane.

Figure 4:
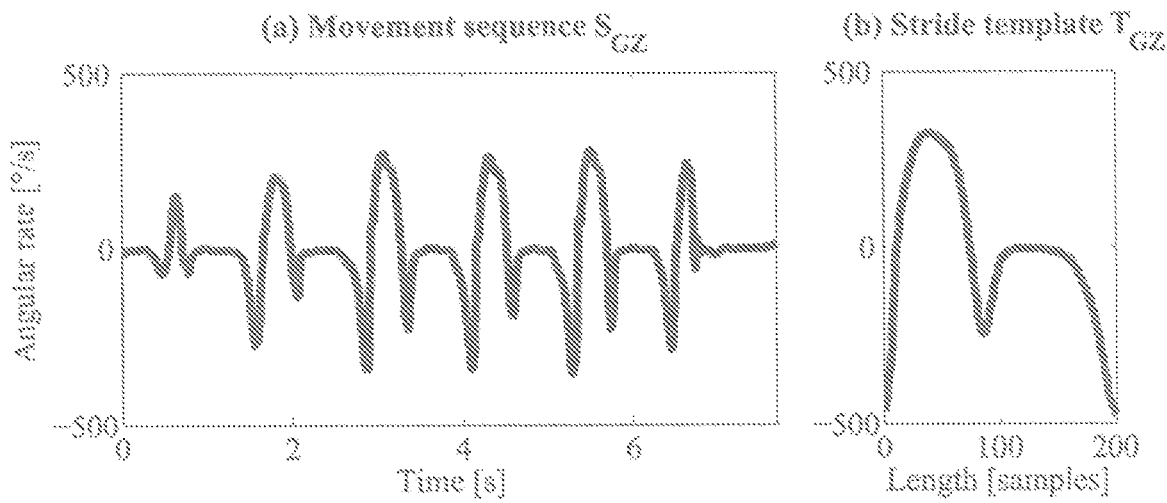

FIG. 4: (a): the movement sequence $S_{GZ}$ shows a typical angular rate representation of a gait sequence in the sagittal plane (GZ); (b): the stride template $T_{GZ}$ shows the template of the corresponding axis, which was used for stride segmentation in the appended example.

Figure 5:
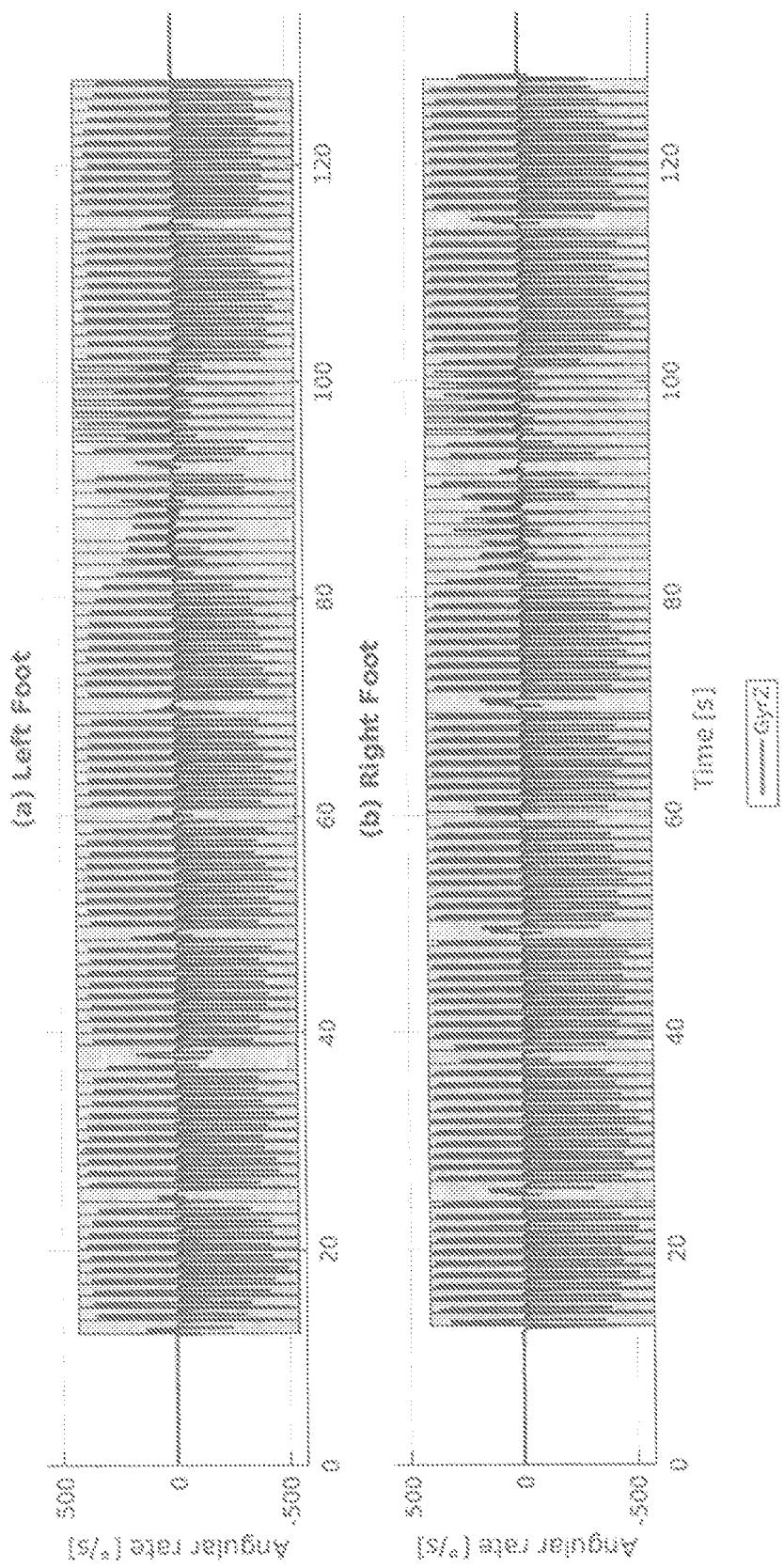

FIG. 5: Shown is the GZ gyroscope data of FIG. 2 after stride segmentation. The beginning and end of data segments representing strides are represented by lines. The area from seconds 80 to 100 includes stairway walking and the areas with low amplitude turning sequences. Other not segmented areas in the beginning and end of the signal sequence include gait pause.

FIG. 6a: Shown is an exemplary data segment representing a stride resulting from stride segmentation. Furthermore, the positions of the stride events heel-strike, mid-stance and toe-off in the respective data segment are indicated. The detailed position of the stride events was determined as described elsewhere herein. Shown is the data of the X and GZ axes. As the data of the X axis was measured with the accelerometer unit of the sensor and the data of the GZ axis was measured with the gyroscope unit of the sensor the measured scales and units are different. Therefore the depicted data was normalized with respect to the corresponding sensor ranges.

FIG. 6b: Schematic drawing illustrating the definition of toe off, mid stance and heel strike events.

FIG. 7: Three segmented strides from left foot with TO (toe-off), HS (heel-strike) and MS (mid-stance) events of a typical gait signal (O: toe-off; +: heel-strike; x: mid-stance). The depicted "data segments" show the areas/data segments representing respective strides which are the direct output of the stride segmentation algorithm. HS-HS (from heel strike to heel strike) segments and MS-MS (from mid-stance to mid-stance) segments are alternative (first and second) data segments representing the strides on the basis of different stride definitions. The numbers behind the "data segment" HS-HS segment" and "MS-MS segment" indicate the number of the respective stride to which the indicated data segment is assigned. The reason of defining different data segments representing a single stride is that different data segments representing a stride are advantageous for determining different stride features. The HS-HS segments are, for example, preferably used to determine e.g. stride times. The MS-MS segments are, for example, preferably used to determine e.g. the stride length. It is important to note that different data segments assigned to the same stride (due to different stride definitions) may be utilized during further analysis.

Figure 8:
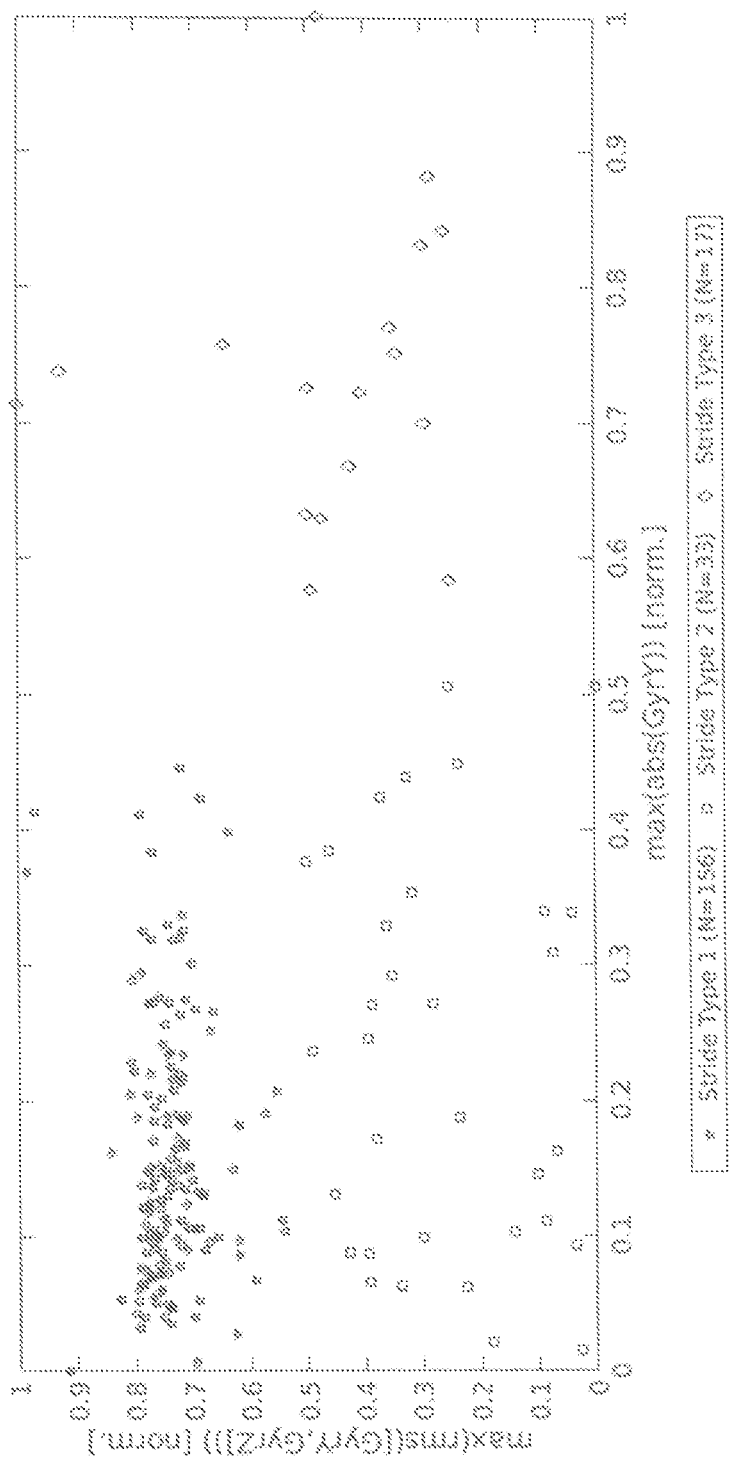

FIG. 8: Shown are the results of clustering the strides identified within the test gait sequence shown in FIG. 2. The depicted clustering has been performed with the k-means clustering algorithm on two exemplary generic stride features. Specifically, clustering was performed with the two generic stride features the maximum of the absolute value of gyroscope y-axis signal (GY) (x-axis in the shown plot) and the maximum of RMS values of gyroscope y- and z-axis (GY, GZ) (y-axis of the shown plot) Evaluation of the clustering performance was performed with the silhouette index.

Figure 9:
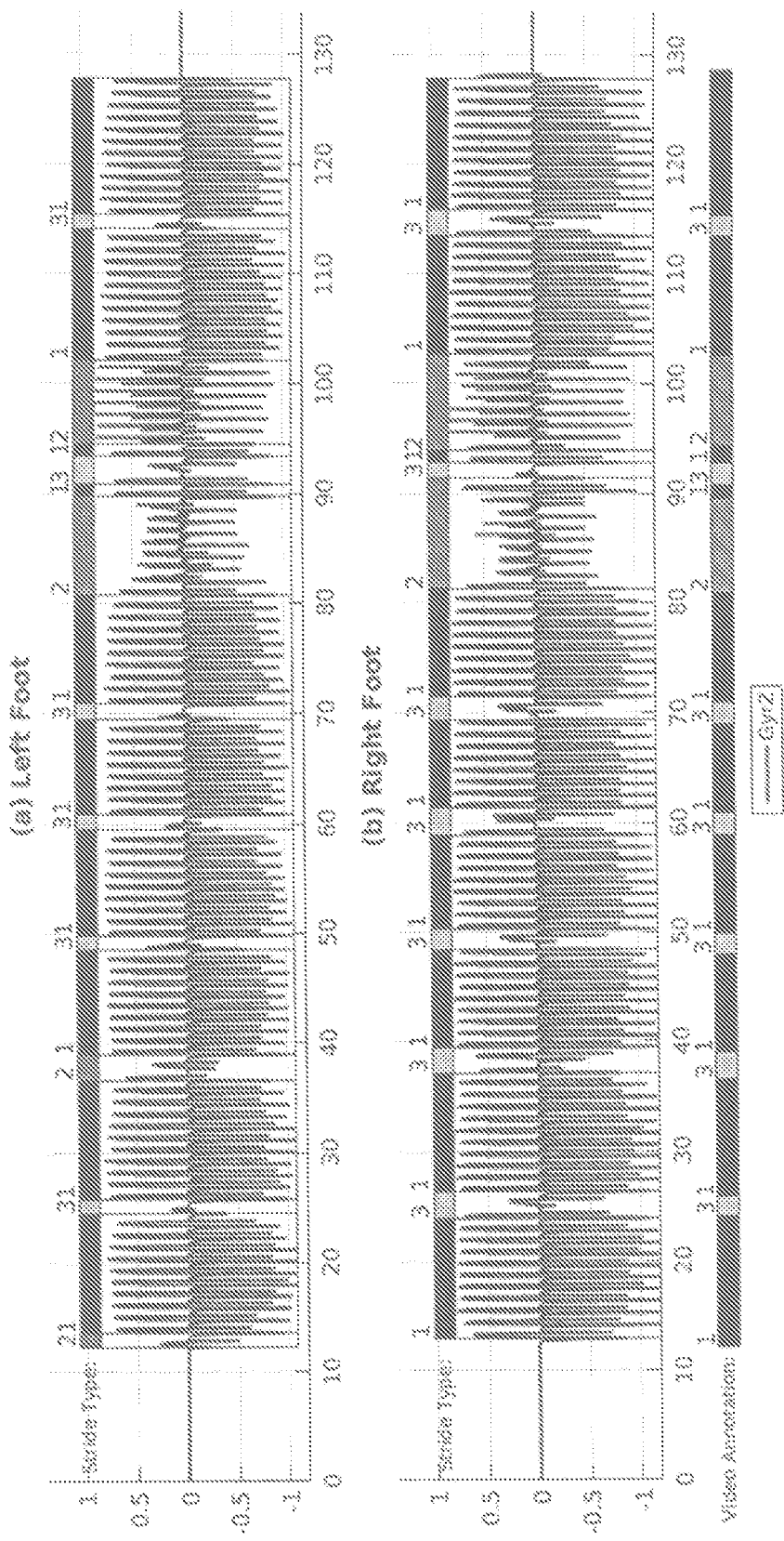

FIG. 9: Shown are the stride clusters/groups within the test gait sequence shown in FIG. 2 that correspond to the identified stride types (as indicated by the same numbers as used in FIG. 8 and a corresponding grey scale code in the bars at the top of the signals of the right and left foot, respectively; the grey scale code is explained further below) from clustering shown in FIG. 8. Additionally shown is a corresponding reference assignment (as a bar below the data of the feet) to the stride types/classes that was manually achieved from a corresponding video recording of the same gait sequence. As the gait sequence analyzed comprised purposeful stride types, the manual assessment using the video recording could serve here as a respective reference for assessing the clustering performance. Light-gray: turning strides (3); gray: walking stairways (2); dark-gray: straight walk (1).

Figure 10:
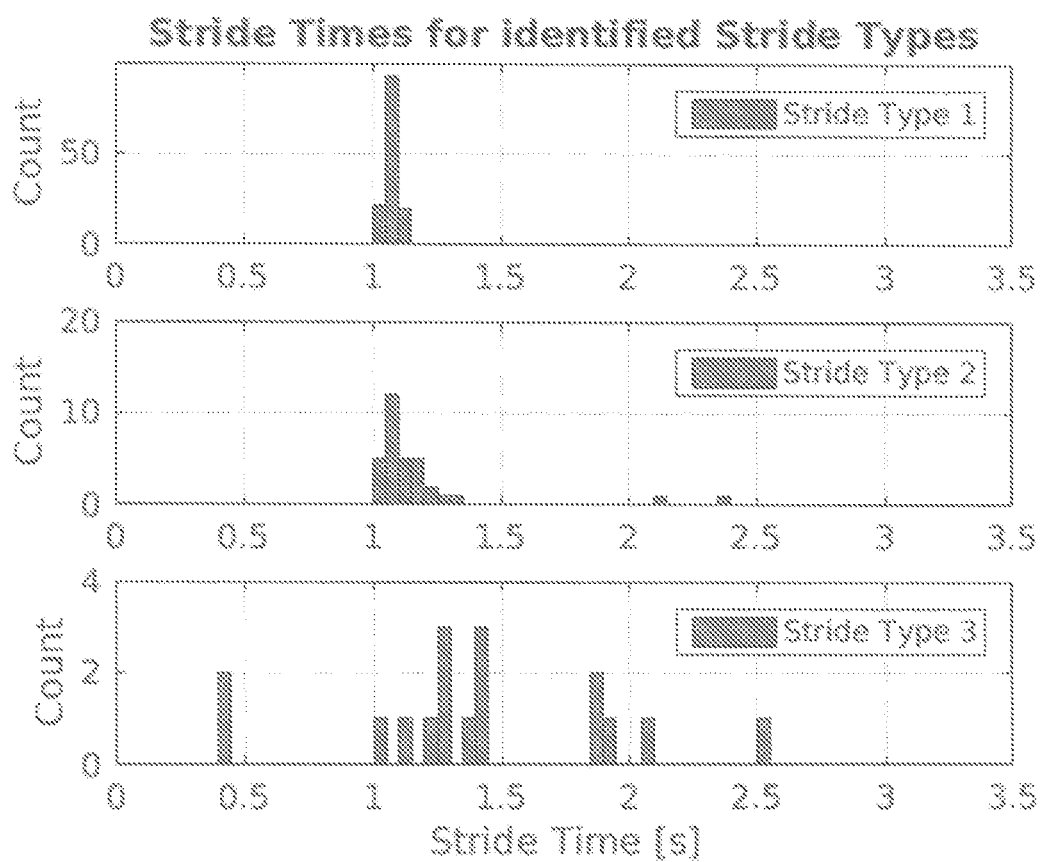

FIG. 10: Shown are histograms that depict for each of the three individual stride types/classes identified by clustering (see FIG. 8) the distribution of the stride times of the strides of the respective classes/clusters. The count indicates the number of strides with a certain stride time. Stride types 1, 2 and 3 correspond to the stride types/classes of FIG. 8.

Figure 11:
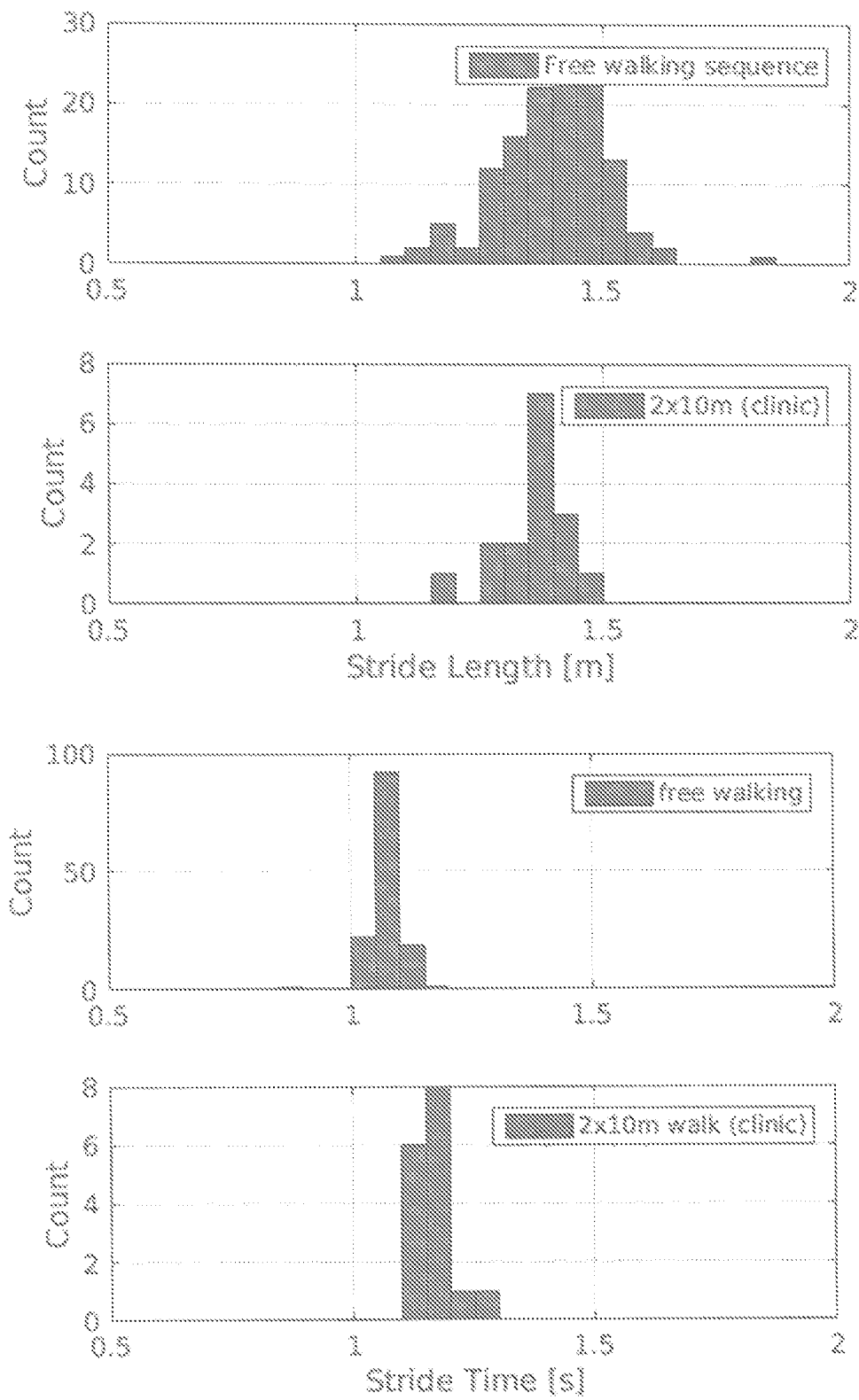

FIG. 11: Shown are histograms that compare the distribution of stride length (see two upper histograms) and stride time (see two lower histograms) between the strides of free walking (stride type/class 1) as determined by the clustering approach according to the method of the present invention (see FIG. 8) and a clinical 2×10 m walk as currently used in clinic settings (acquired with the same system but without clustering).

The following non-limiting Examples describe and/or illustrate the invention.

EXAMPLE 1

The following non-limiting example illustrates a method for analyzing gait of a subject according to the present invention.

Recording Sensor Data

In a first step sensor data representing the 3D-movements of both feet of a healthy man with an age of 27 years was acquired simultaneously over a time segment of about 134 seconds. During the recording of the 3D-movement data the man was walking so that the acquired sensor data comprises a plurality of strides of both feet. The content in the 3D-movement data corresponds to six phases of straight walking, divided by turnings, walking up a flight of stairs, turning on the landing, walking down a flight of stairs followed by 2 straight walking phases divided by a turn. Additionally, a 2 times 10 meter walk, a standardized clinical gait test, including 2 straight walking phases divided by a turn was acquired for the same subject.

The data was acquired with a sensor system, referred to as eGaIT system (Kanzler et al., 2015, 2015 37th Annual International Conference of the IEEE Engineering in Medicine and Biology Society (EMBC) pp. 5424-5427). The eGaIT system is an inertial sensor measurement system, which consists of two sensor units attached on the lateral side of both shoes (see FIG. 1). The sensor units Shimmer 3® were developed from Shimmer sensing (Dublin, Ireland) and include a tri-axial (3D) gyroscope (InvenSense MPU9150, range of ±1000°/s, sensitivity of 16LSB/°s) and a tri-axial (3D) accelerometer (STMicroelectronics, LSM303DLHC, range of ±8 g, sensitivity of 83LSB/g) (Burns et al., 2010, IEEE Sensors Journal 10: pp. 1527-1534). The data was recorded wirelessly via Bluetooth with a sampling rate of 102.4 Hz. Both sensor units were mounted in a position of the shoes (see FIG. 1) located below the ankle joints of the test subject in a worn state. As described by Peruzzi et al., this sensor position is well suited for determining distinct spatio-temporal stride features from the measured data (Peruzzi et al., 2011, Journal of Biomechanics 44: pp. 1991-1994). Thus, this sensor position is particularly well-suited for providing data suitable for a method for gait analysis according to the present invention.

Preprocessing of the Recorded Sensor Data

Axes Alignment

In the present example sensor signals for both feet of the subject were acquired simultaneously. No filtering for accelerometer and gyroscope signals was applied. For the accelerometer the x-axis was defined as the anterior-posterior movement (AX), the y-axis as the inferior-superior movement (AY) and the z-axis as the lateral-medial movement (AZ) (see FIG. 1a). In the case of the angular velocities of the gyroscope data, the rotations were defined as GX in the coronal plane around the x-axis, as GY in the transverse plane around the y-axis and as GZ in the sagittal plane around the z-axis (see FIG. 1b).

Accordingly, to obtain an equal sensor orientation for the left and the right sensor unit, sensor signals were preprocessed. Specifically, the orientation of the left sensor unit was taken directly from the hardware and is defined as described in FIG. 1. Due to opposite sensor unit mounting, axes of the right sensor unit were inverted to get comparable signals and maintain the algebraic sign of the data. Following axes were inverted: AX: anterior-posterior movement; GY: angular rate in transverse plan and GZ: angular rate in sagittal plane.

Conversion of the Raw Sensor Data

The raw sensor data was measured in mV. Accordingly, the aligned sensor data was next converted into accelerometer data (in m/s$^2$) and to gyroscope data (in °/s), respectively. The conversion of the sensor data was achieved by a method described by Ferraris and coworkers (Parvis and Ferraris, 1995, Sensors and Materials 7: pp. 311-330). In brief, the sensor raw data calibration described by Ferraris and coworkers consists of the determination of the bias, scale factor and orientation of the sensors. To determine these factors only a set of standardized rotations and static measurements needs to be performed. The bias is a simple additive constant for each axis of accelerometer or gyroscope. Depending on the sensor range the scaling matrix is needed to scale the raw outputs to the usually used units. With the measured orientation the impact of the linear acceleration on the gyroscope sensor output can be corrected. To record calibration files for the method of Ferraris and coworkers, static measurements on each side of the sensor and 360° rotations around the three axes have been performed.

Results of Preprocessing

The output resulting from the two above-mentioned preprocessing steps of the raw sensor data is exemplary illustrated in FIGS. 2 and 3. FIG. 2 shows the preprocessed GZ gyroscope data of the left and the right foot. FIG. 3 shows sections of the preprocessed data of all three accelerometer (see FIGS. 3A to C) and all three gyroscope axes (see FIGS. 3D to E) of the left foot. Shown is a representative time section, which comprises a data segment representing about four strides.

Identifying Data Segments Representative for Strides Within the 3D-Movement Data Next, data segments, which represent a single stride/stride cycle, were identified within the preprocessed sensor data.

Stride Segmentation

In a first step data segments representing single strides were identified within the preprocessed sensor data by a process referred to as automated stride segmentation. The automated stride segmentation was performed using a multidimensional subsequence dynamic time warping (msDTW) approach as, for example, described by Barth, Oberndorfer et al. (Barth et al., 2015, MDPI Sensors 15: pp. 6419-6440).

In brief, a predefined template data segment (see FIG. 4*b*; right panel), which is representative for a single stride, was compared to the preprocessed sensor signal (see FIG. 4*a*) using msDTW. With the used algorithm it is possible to use a template for one stride and all available axes (in the present example only GZ was used). A similarity measure that measures the similarity between signal and template was calculated, as defined in Barth, Oberndorfer et al. (Barth et al., 2015, MDPI Sensors 15: pp. 6419-6440). If this similarity measure was above a defined threshold (in the present example 42), a data segment representative for a stride was detected. The major advantage of using msDTW is its time invariance, which allows for using msDTW for stride segmentation from data corresponding to movement sequences comprising strides that vary in time or speed. In principle, however also all other methods mentioned above could be used for stride segmentation.

The template data segment used for the msDTW in the present example (see FIG. 4*b*) was predefined based on a previously recorded reference data set. Specifically, the template was generated by manually identifying and segmenting data segments representative for strides in said reference data set, which comprised 3D-movement data of gait sequences of 25 elderly volunteers that was acquired with the same sensor system as used in the present example. Specifically, in the reference data set in total 681 data segments representing strides were manually identified and segmented. The manual identification and segmentation of the strides, in particular, comprised defining the start and the end time (within the time axis) of each step within the recorded data; i.e. the manual definition of the data segments representing strides. In the present example the identification of start and end values in the time axis defining the start and end of a respective data segment in the time axis was performed using the angular rate in the sagittal plane (GZ axis). In principle, also the data of any of the other data axes could have been used.

As mentioned elsewhere herein, data segments with different start and end points of a stride cycle can be assigned to each stride. For the template definition from the reference data set, two consecutive negative peaks in the sagittal plane angular rate data axis (GZ) were defined as start and end point of each data segment representing a single stride. Using two consecutive negative peaks in the angular rate as start and end point has the advantage of allowing a very robust and accurate manual definition of the start and end point.

The manually identified start and end points of the segmented strides in the time axis defined by using the GZ axis data also allowed to define the corresponding data segments representing the strides in the other data axes (as the time axis is identical for all six data axes). After manual identification, the respective templates for the axes were calculated by averaging.

In the present example the templates defined for the GZ axes was employed for stride segmentation in the recorded data. However, alternatively, or in addition, corresponding templates for other data axes (e.g. AX, AY, AZ, GX, GY) could have been used for stride segmentation.

The result of stride segmentation with the msDTW algorithm was a set of tuples containing the start and end samples of n segmented strides (n=206). In other words, strides were identified and a corresponding starting time and end time of a data segment representing said strides was determined. These start and end times of the identified strides define the start and end point of respective data segments representing single strides in all three gyroscope planes and accelerometer axes. Accordingly, as a result of the stride segmentation data segments each being representative for a stride were determined in all three gyroscope (GX, GY, GZ) and all three accelerometer (AX, AY, AZ) data sets. In the present example data segments being representative for strides were identified for all 6 axes. Depending on the further analysis, it may, however, be in general sufficient to segment only some of the data corresponding to the six degrees of freedom.

FIG. 5 exemplary shows the result of the stride segmentation by msDTW for the GZ axes data of the right and the left foot recorded during the recorded gait sequence of the man. The data sections comprising data segments representing strides are highlighted in gray. The start and end time of each data segment representing a stride within the gray sections are represented by lines. The other data sections, which are not highlighted in gray, represent other movements as strides. In the data shown in FIG. 5, these represent only standing phases in the beginning and end of the signal.

In the present example, for the subsequent analysis and to calculate stride features specifically only such strides, which belong to a series of at least two consecutive strides, were taken into account.

Definition of Stride Events and Data Segments Representing the Identified Strides In the next step, stride events were detected within the data segments of all strides selected for further analysis. In particular, the heel-strike, toe-off and mid-stance events were determined as described by Rampp and coworkers (Rampp et al., 2014, IEEE Transactions on Biomedical Engineering 62: pp. 1089-1097). In brief these stride events were determined as follows:

The toe-off (TO) event was defined as the zero crossing of the angular rate in sagittal plane (GZ) within each data segment representing an identified stride.

At mid-stance the foot has the lowest velocity. The gyroscope signal holds the most reliable information for low velocity during walking. For that reason a "Angular Rate Energy Detector (ARE)" (Skog et al., 2010, Indoor Positioning and Indoor Navigation (IPIN), 2010 International Conference on pp. 1-6) is used to detect mid-stance events.

The heel-strike (HS) event was defined between the absolute maximum and the end of the first half of the gyroscope's sagittal plane signal. Within this segment, the HS event was found by searching for the minimum between the point of the steepest negative slope and the point of steepest positive slope in that signal segment. In that signal segment the anterior-posterior signal of the accelerometer was searched for a minimum in the area 50 ms before and 20 ms after the described minimum in the gyroscope signal. The minimum in the anterior-posterior signal of the accelerometer was defined as the HS event.

FIG. 6 exemplifies the definition of the toe-off, mid-stance and heel-strike event based on one data segment gained by stride segmentation.

The definition of the above-mentioned stride events allowed determining for each of the selected strides next to the initially identified data segment (during stride segmentation) further data segments representing the same. In particular, a data segment in which the start and the end point are defined by two consecutive heel-strike events (HS-HS segment) or two consecutive mid-stance events (MS-MS segment) were defined for each stride. FIG. 7 exemplary illustrates how the respective data segments are defined and assigned to the respective strides. The additional data segments (the HS-HS segment and the MS-MS segments) representing the strides have the advantage of being particularly well suited for determining a variety of distinct stride features (in particular biomechanical stride features).

Determining Stride Features

Next biomechanical and generic stride features were determined for each of the selected strides using the data segments or stride events representing the same. In the present example, these included the spatio-temporal parameters stride length and stride time and the generic features RMS(GY), RMS(GZ) and the absolute maximum of the GY channel max(|GZ|). For explicit definitions of these features, the reader is referred to the main body of the text.

Defining Clusters of Strides Based on Generic Stride Features

Next, the selected strides were exemplary clustered into stride classes/types based on two of the determined generic stride features, in particular the maximum of the absolute value of gyroscope y-axis signal (GY axis signal) and the maximal RMS value over the gyroscope y- or z-axis signal.

In the present example, the k-means clustering algorithm (MacQueen, 1967, Proceedings of the fifth Berkeley symposium on mathematical statistics and probability 1: pp. 281-297) has been used. For clustering, only 2 generic features (as mentioned above) were taken into account in order to demonstrate that already two of the stride features can discriminate between different stride types. Evaluation of the clustering performance for different values of k, was performed with the silhouette index (Rousseeuw, 1987, Journal of Computational and Applied Mathematics 20: pp. 53-65). In computing the silhouette index, one compares the average dissimilarities of a given data-point to others from its cluster to average dissimilarities of the same object to other clusters and tries to maximize this difference. The k with the best silhouette index determined the number of cluster, i.e. stride classes/types, found in the current example.

As shown in FIG. 8, the clustering using only two generic features already gives good results regarding the separation into the three stride types straight walking, turning and walking on stairways on the left and right foot. The corresponding stride sequences in the 3D-movement data shown in FIG. 2 are shown in FIG. 9 with overlaid stride clusters and a manual reference annotation obtained from a corresponding video recording of the same sequence of strides. The video recording was performed in parallel to the sensor-based gait analysis. The annotation derived from the video is a manual/visual assessment (which is very accurate in the present case in which the gait sequence comprised purposeful stride types and, thus, allowed to evaluate the power of the clustering performance afterwards) which of the stride type classes the respective strides belonged to. The identified stride classes separate the straight walking phases from turnings and walking on stairways and thereby recover the actually recorded data nearly perfectly. The only wrongly assigned strides are the first stride and the second turn on the left foot (compare FIG. 9 at t=12 s and t=37 s) that are falsely assigned to the walking on stairways cluster. Additionally, one stride on the right foot is wrongly assigned to the stairway walking class although it should have been a straight stride (compare FIG. 9 at t=91 s). The wrongly labeled/clustered turning stride on the left foot and straight stride on the right foot actually lie on the border between wrongly assigned and the correct class in the feature representation shown in FIG. 8 and a correct labeling/clustering can be achieved by using a third feature in the clustering that further discriminates between the corresponding classes, e.g. the entropy of the gyroscope Y-axis (GY). Regarding the first stride on the left foot, this is actually an initiation stride and we have very few examples of this stride class in the current movement sequence. Here, correct labeling/clustering can, however, be achieved by longer and thereby richer movement sequences in terms of the stride classes captured. Furthermore, using additional stride features for clustering can also improve the discrimination between initiation strides and other movement classes.

It is also important to note that any other combination of two or more stride features could have been used for clustering and would result in clustering results of similar quality given that the computed features are discriminative between the stride classes of interest.

The advantage of the method in the present invention is that each of the identified classes can be used to calculate and analyze stride features in more detail. The previously described stride segmentation method, which was also employed in one step of the method used in the present example is in principle also able to filter out straight walking phases if used with a different, more stringent threshold and axes combination. However, all other stride classes would be rejected (not identified) and only an analysis of the straight walking would be possible. This is due to the fact that the template used for segmentation is defined from a straight walking sequence. Turning strides, for example, exhibit large variability and it is thus hard to define one template that could be used to segment all possible turning movements from a movement sequence in order to analyze turnings. Segmenting all strides in movement sequence in the first place and then sorting them in different stride types depending on their characteristics, thus enables a much richer, stride-type-specific analysis of the data. In particular, different stride types can be identified and grouped with a single stride template for stride segmentation.

Stride Analysis and Interpretation of Strides Per Stride Class/Type

The stride class/type 1 comprises the most strides and, thus, can be defined as the most frequent or typical stride class of the subject. In this example stride class 1 includes only straight walking. This first class of strides is characterized by an average stride time of 1.07±0.03 s ($\mu \pm \sigma$, left and right foot combined). The second stride class, however, has an average stride time of 1.19±0.28 s. Thus, the second stride class represents slower and more irregular strides compared to the typical stride of the test person. In this example the second class represents strides during walking on stairway, which can, in principle give additional information on the ability or impairment of the assessed subject compared to walking on flat ground, also correlating to the fitness, immobility, and/or autonomy of the subject. The third stride class (turning strides) comprises strides that have an average stride time of 1.41±0.54 s. An increased number, time and variability of turning strides e.g. in Parkinson's disease might represent measures for disease progression, but also for limitations of mobility and/or increased risk of falling. If all strides are taken together without the clustering, the average stride time is 1.12±0.22 s. As most of the strides of the analyzed gait sequence were strides of straight walking, the mean value of stride time gained without clustering is closest to the mean value of the first cluster. However, the determined value has a much higher variance. The method of the present invention including clustering of strides by one or more stride features, thus allows for reducing the variance of the determined stride time of the most frequent strides (in this case straight walking). Furthermore, by clustering also the mean stride time for the other stride types (here strides on stairways and turning strides) could be determined. In particular, the mean stride time detected for the turning strides is different from the other strides. Thus, identifying these strides by clustering allows characterizing the characteristics of these strides (such as the stride time) independent of the other strides.

FIG. 10 gives an overview on the distributions of stride times in the individual stride classes. The heterogeneity of each cluster was further assessed in terms of the average pairwise Euclidean distance in the two-dimensional feature space between elements from the same cluster (compare FIG. 8). Since the two statistical features used in this example were normalized prior to clustering, the heterogeneity index is dimensionless as well and ranges between 0.0 and $\sqrt{2}$. The clustering of strides improves the heterogeneity in all clusters compared to an evaluation on all strides and therefore shows the benefit of a clustering approach: Identifying similar strides prior to analyzing a gait sequence reduces variability in the data by sorting it into different stride types. This allows deduction of an individual gait profile (number of distinct stride types, their frequency and stride characteristics).

Furthermore, the heterogeneity index also ranks the clusters in the correct order such that the most prominent stride class 1 gets the best heterogeneity score:

|  | Stride time [s] (mean ± standard deviation) | Heterogeneity | N [strides] |
| --- | --- | --- | --- |
| Class 1 | 1.07 ± 0.03 | 0.104 | 156 (or 76%) |
| Class 2 | 1.19 ± 0.28 | 0.124 | 33 (or 16%) |
| Class 3 | 1.41 ± 0.54 | 0.171 | 17 (or 8%) |
| All strides | 1.12 ± 0.22 | 0.310 | 206 (or 100%) |

Comparing Strides from Free Walking to Standardized Gait Tests

With the identification of typical strides of a person (stride class/type 1) from free walking it is possible to compare data from free walking acquisitions to standardized clinical gait tests like the 2×10 meter walk (which simulates a short sequence of straight walking). If we compare stride length from free walking sequence to a 2×10 meter walk completed by the same subject, we can observe more normally distributed stride lengths in the free walking data (FIG. 11). If one does not reach a normal distribution for a parameter in a given movement sequence, one could argue that extraction of mean values and standard deviations might be ill-posed and more data has to be acquired for meaningful statistical analysis. Such a concept could also be integrated in the data recording by iteratively segmenting and clustering the strides in already acquired data until normal distributions are reached in the desired parameter set. In other words, the developed algorithms can determine when there is enough data for a meaningful analysis.

|  | Stride time [s] (mean ± standard deviation) | N [strides] |
| --- | --- | --- |
| Free walking | 1.07 ± 0.03 | 156 |
| 2 × 10 meter | 1.16 ± 0.34 | 16 |

Therefore, the present example illustrates that a method according to the present invention can reliably cluster strides within a gait sequence. Moreover, it demonstrates that already two generic stride features are sufficient to define robust clusters representing stride classes/types within such a movement sequence. Additionally, the clustering allows drastically reduction in the variability on the mean stride features and with that characterizing the gait of the test person in more detail by introducing mean stride features per stride type.

REFERENCES CITED HEREIN

Amboni, M., Barone, P., Iuppariello, L., Lista, I., Tranfaglia, R., Fasano, A., Picillo, M., Vitale, C., Santangelo, G., Agosti, V. et al. (2012). Gait patterns in parkinsonian patients with or without mild cognitive impairment. *Movement disorders: official journal of the Movement Disorder Society* 27, 1536-43.

Arel, I., Rose, D. and Karnowski, T. (2010). Deep machine learning-A new frontier in artificial intelligence research. *IEEE Computational Intelligence Magazine* 5, 13-18.

Barth, J., Oberndorfer, C., Pasluosta, C., Schülein, S., Gassner, H., Reinfelder, S., Kugler, P., Schuldhaus, D., Winkler, J., Klucken, J. et al. (2015). Stride Segmentation during Free Walk Movements Using Multi-Dimensional Subsequence Dynamic Time Warping on Inertial Sensor Data. *MDPI Sensors* 15, 6419-6440.

Bishop, C. (2001). Bishop Pattern Recognition and Machine Learning, (ed.: Springer, New York.

Burns, A., Greene, B. R., McGrath, M. J., O'Shea, T. J., Kuris, B., Ayer, S. M., Stroiescu, F. and Cionca, V. (2010). SHIMMER™—A Wireless Sensor Platform for Noninvasive Biomedical Research. *IEEE Sensors Journal* 10, 1527-1534.

Chen, X.-w. and Lin, X. (2014). Big Data Deep Learning: Challenges and Perspectives. *IEEE Access* 2, 514-525.

Cybenko, G. (1989). Approximation by superpositions of a sigmoidal function. *Mathematics of control, signals and systems* 2, 303-314.

Day, W. H. E. and Edelsbrunner, H. (1984). Efficient algorithms for agglomerative hierarchical clustering methods. *Journal of Classification* 1, 7-24.

Dempster, A. P., Laird, N. M. and Rubin, D. B. (1977). Maximum likelihood from incomplete data via the EM algorithm. *Journal of the royal statistical society. Series B (Methodological)*, 1-38.

Duda, R. O., Hart, P. E. and Stork, D. G. (2000). Pattern Classification (2nd Edition). Eskofier, B., Oleson, M., DiBenedetto, C. and Hornegger, J. (2009). Embedded surface classification in digital sports. *Pattern Recognition Letters* 30, 1448-1456.

Georgescu, B., Shimshoni, I. and Meer, P. (2003). Mean shift based clustering in high dimensions: a texture classification example. In *Computer Vision, 2003. Proceedings. Ninth IEEE International Conference on*, (ed., pp. 456-463 vol. 1.

Greene, B. R., Foran, T. G., McGrath, D., Doheny, E. P., Burns, A. and Caulfield, B. (2012). A comparison of algorithms for body-worn sensor-based spatiotemporal gait parameters to the GAITRite electronic walkway. *Journal of applied biomechanics* 28, 349-55.

Guha, S., Rastogi, R. and Shim, K. (1998). CURE: an efficient clustering algorithm for large databases. *SIGMOD Rec.* 27, 73-84.

Hollman, J. H., Childs, K. B., McNeil, M. L., Mueller, A. C., Quilter, C. M. and Youdas, J. W. (2010). Number of strides required for reliable measurements of pace, rhythm and variability parameters of gait during normal and dual task walking in older individuals. *Gait & Posture* 32, 23-28.

Horak, F. B. and Mancini, M. (2013). Objective biomarkers of balance and gait for Parkinson's disease using body-worn sensors. *Movement disorders: official journal of the Movement Disorder Society* 28, 1544-51.

Jain, A. K., Murty, M. N. and Flynn, P. J. (1999). Data clustering: a review. *ACM computing surveys (CSUR)* 31, 264-323.

Jarchi, D., Wong, C., Kwasnicki, R. M., Heller, B., Tew, G. A. and Yang, G.-Z. (2014). Gait Parameter Estimation From a Miniaturized Ear-Worn Sensor Using Singular Spectrum Analysis and Longest Common Subsequence. *IEEE Transactions on Biomedical Engineering* 61, 1261-1273.

Kanzler, C. M., Barth, J., Rampp, A., Schlarb, H., Rott, F., Klucken, J. and Eskofier, B. M. (2015). Inertial Sensor based and Shoe Size Independent Gait Analysis including Heel and Toe Clearance Estimation. In *2015 37th Annual International Conference of the IEEE Engineering in Medicine and Biology Society (EMBC)* (ed., pp. 5424-5427.

Klucken, J., Barth, J., Kugler, P., Schlachetzki, J., Henze, T., Marxreiter, F., Kohl, Z., Steidl, R., Hornegger, J., Eskofier, B. et al. (2013). Unbiased and Mobile Gait Analysis Detects Motor Impairment in Parkinson's Disease. *PLoS ONE* 8, e56956.

Lapedes, A. S. and Farber, R. M. (1988). How neural nets work. In *Neural information processing systems*, (ed., pp. 442-456.

Lord, S., Galna, B. and Rochester, L. (2013). Moving forward on gait measurement: Toward a more refined approach. *Movement disorders: official journal of the Movement Disorder Society* 28, 1534-43.

MacQueen, J. (1967). Some methods for classification and analysis of multivariate observations. In *Proceedings of the fifth Berkeley symposium on mathematical statistics and probability*, vol. 1 (ed., pp. 281-297: Oakland, Calif., USA.

Mannini, A. and Sabatini, A. M. (2012). Gait phase detection and discrimination between walking-jogging activities using hidden Markov models applied to foot motion data from a gyroscope. *Gait & Posture* 36, 657-61.

Mariani, B., Hoskovec, C., Rochat, S., Büla, C., Penders, J. and Aminian, K. (2010). 3D gait assessment in young and elderly subjects using foot-worn inertial sensors. *Journal of Biomechanics* 43, 2999-3006.

Mariani, B., Jiménez, M. C., Vingerhoets, F. J. G. and Aminian, K. (2013). On-shoe wearable sensors for gait and turning assessment of patients with Parkinson's disease. *IEEE transactions on bio-medical engineering* 60, 155-8.

McDonough, a. L, Batavia, M., Chen, F. C., Kwon, S. and Ziai, J. (2001). The validity and reliability of the GAITRite system's measurements: A preliminary evaluation. *Archives of Physical Medicine and Rehabilitation* 82, 419-25.

Muro-de-la-Herran, A., Garcia-Zapirain, B. and Mendez-Zorrilla, A. (2014). Gait analysis methods: an overview of wearable and non-wearable systems, highlighting clinical applications. *Sensors (Basel, Switzerland)* 14, 3362-94.

Ngo, T. T., Makihara, Y., Nagahara, H., Mukaigawa, Y. and Yagi, Y. (2015). Similar gait action recognition using an inertial sensor. *Pattern Recognition* 48, 1289-1301.

Parvis, M. and Ferraris, F. (1995). Procedure for effortless in-field calibration of three-axial rate gyro and accelerometers. *Sensors and Materials* 7, 311-330.

Perry, J. (1992). Gait analysis. *Normal and pathological function* 1.

Peruzzi, A., Della Croce, U. and Cereatti, A. (2011). Estimation of stride length in level walking using an inertial measurement unit attached to the foot: A validation of the zero velocity assumption during stance. *Journal of Biomechanics* 44, 1991-1994.

Rampp, A., Barth, J., Schülein, S., Gaßmann, K.-G., Klucken, J. and Eskofier, B. M. (2014). Inertial Sensor Based Stride Parameter Calculation from Gait Sequences in Geriatric Patients. *IEEE Transactions on Biomedical Engineering* 62, 1089-1097.

Rebula, J. R., Ojeda, L. V., Adamczyk, P. G. and Kuo, A. D. (2013). Measurement of foot placement and its variability with inertial sensors. *Gait & Posture* 38, 974-980.

Roiz, R. D. M., Cacho, E. W. A., Pazinatto, M. M., Reis, J. G., Cliquet, A. and Barasnevicius-Quagliato, E. M. A. (2010). Gait analysis comparing Parkinson's disease with healthy elderly subjects. *Arquivos de neuropsiquiatria* 68, 81-86.

Rousseeuw, P. J. (1987). Silhouettes: A graphical aid to the interpretation and validation of cluster analysis. *Journal of Computational and Applied Mathematics* 20, 53-65.

Roy, S. and Bhattacharyya, D. (2005). An approach to find embedded clusters using density based techniques. In *Distributed computing and internet technology*, pp. 523-535: Springer.

Salarian, A., Russmann, H., Vingerhoets, F. J. G., Dehollain, C., Blanc, Y., Burkhard, P. R. and Aminian, K. (2004). Gait assessment in Parkinson's disease: toward an ambulatory system for long-term monitoring. In *IEEE Transactions on Biomedical Engineering*, vol. 51 (ed., pp. 1434-1443.

Shannon, C. E. (1948). The mathematical theory of communication. 1963. *MD computing computers in medical practice* 27, 306-17.

Skog, I., Nilsson, J.-O. and Handel, P. (2010). Evaluation of zero-velocity detectors for foot-mounted inertial navigation systems. In *Indoor Positioning and Indoor Navigation (IPIN), 2010 International Conference on*, (ed., pp. 1-6: IEEE.

Trojaniello, D., Cereatti, A., Pelosin, E., Avanzino, L., Mirelman, A., Hausdorff, J. M. and Della Croce, U. (2014). Estimation of step-by-step spatio-temporal parameters of normal and impaired gait using shank-mounted magneto-inertial sensors: application to elderly, hemiparetic, parkinsonian and choreic gait. *Journal of NeuroEngineering and Rehabilitation* 11, 152.

Vieregge, P., Stolze, H., Klein, C. and Heberlein, I. (1997). Gait quantitation in Parkinson's disease? locomotor disability and correlation to clinical rating scales. *Journal of Neural Transmission* 104, 237-248.

Webster, K. E., Wittwer, J. E. and Feller, J. A. (2005). Validity of the GAITRite® walkway system for the measurement of averaged and individual step parameters of gait. *Gait & Posture* 22, 317-321.

Windolf, M., Götzen, N. and Morlock, M. (2008). Systematic accuracy and precision analysis of video motion capturing systems-exemplified on the Vicon-460 system. *Journal of Biomechanics* 41, 2776-2780.

Witten, I. H. and Frank, E. (2005). Data Mining: Practical machine learning tools and techniques: Morgan Kaufmann, Elsevier.

The invention claimed is:

1. A method for analyzing gait of a subject, the method comprising:
   (a) generating, from 3D-accelerometers and/or 3D-gyroscopes mounted on a left foot and a right foot, or a left shoe and a right shoe of the subject, data representing 3D-movement of the left foot and the right foot of the subject over time, wherein the 3D-movement comprises a plurality of strides of the left foot and the right foot;

(b) identifying the plurality of strides in the data and defining first data segments for the left foot and the right foot, wherein each of the first data segments comprises one identified stride or a sequence of consecutive identified strides;

(c) determining one or more stride features for each of the first data segments; and (d) defining one or more clusters on the basis of at least one stride feature of the one or more stride features, wherein each cluster represents a class of strides, wherein the one or more clusters are used to determine a gait impairment of the subject.

2. The method of claim 1, wherein defining the first data segments comprises determining at least one gait event selected from a group consisting of heel-strike (HS), mid-stance (MS) and toe-off (TO).

3. The method of claim 1, wherein each of the first data segments represents at most two consecutive strides.

4. The method of claim 1, wherein each of the first data segments comprises exactly two consecutive heel-strike (HS) events and/or exactly two consecutive mid-stance (MS) events.

5. The method of claim 4, wherein each of the first data segments further comprises one or two toe-off (TO) events.

6. The method of claim 1, wherein (b) comprises comparing the data with a predefined data set.

7. The method of claim 1, wherein the one or more stride features are selected from a group consisting of angle course, heel strike angle, toe off angle, clearance course, maximum toe clearance, minimum toe clearance, stride velocity, ground turning angle, medio-lateral sway, double support time, and heel clearance course.

8. The method of claim 1, wherein in (c) determining at least one of the one or more stride features involves a machine learning algorithm.

9. The method of claim 1, wherein (d) comprises clustering the first data segments and/or the identified strides represented by one or more of the first data segments.

10. The method of claim 1, wherein the one or more clusters are used to determine the gait impairment of the subject by performing statistical group separation tests on the one or more clusters for defining the one or more clusters with a certain predefined significance.

11. The method of claim 1, wherein one cluster of the one or more clusters represents a class of typical strides of the subject or wherein one cluster of the one or more clusters represents a class of straight walking strides, walking initiation strides, turning movement strides or stairways walking strides.

12. The method of claim 1, wherein the one or more clusters are used to determine the gait impairment of the subject by generating averaged stride features for at least one or all of the one or more clusters by averaging the one or more stride features over each of the respective one or more clusters.

13. The method of claim 1, wherein the method further comprises identifying second data segments for several or each of the first data segments within one cluster, wherein each of the second data segments represents a stride or an integer number of strides, and wherein the method further comprises concatenating the second data segments in order to generate a 3D-movement sequence comprising several consecutive strides.

14. The method of claim 1, wherein the method further comprises determining an average data segment representing a stride or an integer number of strides for the one or more clusters taking into account several or each of the first data segments per cluster.

15. The method of claim 14, wherein the method further comprises concatenating several of the average data segments of a cluster in order to generate a 3D-movement sequence comprising several consecutive strides.

16. The method of claim 1, wherein (b) involves using an algorithm comprising a Hidden Markov Model algorithm, a Robust event detection algorithm, a Subsequence Dynamic Time Warping algorithm, a Conditional Random Field algorithm, a Longest Common Subsequence algorithm, a Deep Learning algorithm, and/or a Threshold or Matched Filter/Cross-correlation algorithm.

17. The method of claim 1, wherein the one or more stride features are selected from a group consisting of stride time, stride length, swing time, stance time, entropy, mean value, variance, root mean square, minimum, maximum, kurtosis, skewness, dominant frequency, energy in frequency band 0.5 to 3 Hz, energy in frequency band 3 to 8 Hz, energy ratio and signal energy.

18. The method of claim 1, wherein the subject suffers from a neurological disease and wherein the gait impairment is indicative of the neurological disease.

19. The method of claim 1, wherein at least two clusters are defined, and wherein defining the at least two clusters on the basis of the at least one stride feature of the one or more stride features comprises determination of a Dynamic Time Warping distance between the clusters.

20. The method of claim 1, wherein one cluster of the one or more clusters represents a class of typical strides of the subject, and wherein the one cluster is defined as the cluster with the most strides.

21. A system for analyzing gait of a subject, the system comprising:

(a) 3D-accelerometers and/or 3D-gyroscopes adapted to be mounted on a left foot and a right foot, or a left shoe and a right shoe of the subject, and configured to provide data representing 3D-movement of the left foot and the right foot of the subject, wherein the 3D-movement comprises a plurality of strides of the left foot and the right foot; and (b) one or more processing units being configured for:
identifying the plurality of strides in the data and defining first data segments for the left foot and the right foot, wherein each of the first data segments comprises one identified stride or a sequence of consecutive identified strides;
determining one or more stride features for each of the first data segments;
defining one or more clusters on the basis of at least one of the one or more determined stride features, wherein each cluster represents a class of strides; and
determining a gait impairment of the subject using the one or more clusters.

22. The system of claim 21, wherein the system further comprises the left shoe and the right shoe on which the 3D-accelerometers and/or 3D-gyroscopes are mounted.

23. The method of claim 18, wherein the neurological disease comprises Parkinsons or Multiple Sclerosis.

* * * * *